(12) United States Patent
Parsons et al.

(10) Patent No.: US 6,475,142 B1
(45) Date of Patent: Nov. 5, 2002

(54) CURVED STABILIZATION ARM FOR USE WITH SURGICAL RETRACTOR AND TISSUE STABILIZATION DEVICE AND METHODS RELATED THERETO

(75) Inventors: Matthew L. Parsons, Randolph; Trinh D. Phung, Attleboro, both of MA (US); Thomas E. Martin, Riverside; Bruce C. Cathcart, Westerly, both of RI (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/438,670

(22) Filed: Nov. 12, 1999

(51) Int. Cl.$^7$ ................................................ A61B 17/02
(52) U.S. Cl. ....................................... 600/232; 600/228
(58) Field of Search ................................. 600/232, 233, 600/231, 228, 229, 230, 210

(56) References Cited

U.S. PATENT DOCUMENTS

| | | | |
|---|---|---|---|
| 1,460,697 A | * | 7/1923 | Bendlin |
| 2,594,086 A | | 4/1952 | Smith |
| 3,638,973 A | | 2/1972 | Poletti |
| 3,710,783 A | | 1/1973 | Jascalevich |
| 3,858,578 A | | 1/1975 | Milo |
| 4,143,652 A | | 3/1979 | Meier et al. |
| 4,726,356 A | * | 2/1988 | Santilli et al. |
| 4,852,552 A | * | 8/1989 | Chaux |
| 4,949,707 A | | 8/1990 | Levahn et al. |
| 5,167,223 A | | 12/1992 | Koros et al. |

(List continued on next page.)

FOREIGN PATENT DOCUMENTS

| | | |
|---|---|---|
| CA | 2216893 | 2/1999 |
| DE | 297 11 829 | 10/1997 |
| DE | 197 08 587 | 11/1998 |
| EP | 1520832 | 8/1978 |
| EP | 411 586 A1 | 2/1991 |

(List continued on next page.)

OTHER PUBLICATIONS

Izzat, M. Bashar et al., Cardiac Stabilizer for Minimally Invasive Direct Coronary Artery Bypass, Ann. Thorac. Surg., vol. 64, pp. 570–571 (1997).

Riahi, Mohammad et al., A Simple Technique and Device to Provide a Bloodless Operative Field in Coronary Aratery Surgery Without Cross–Clamping the Aorta, Journal of Thoracic and Cardiovascular Surgery, vol. 66, No. 6, Dec. 1973, pp. 974–978.

(List continued on next page.)

*Primary Examiner*—Paul J. Hirsch
(74) *Attorney, Agent, or Firm*—Richard D. Allison; Thomas J. DesRosier

(57) ABSTRACT

The present invention relates to surgical retractors and devices for stabilizing a predetermined area of the body during a surgical procedure, more particularly to surgical retractors and stabilizing devices used in connection with minimally invasive coronary artery bypass grafting surgical procedures, and more specifically to surgical retractors and stabilizing devices especially configured for use with each other for such surgical procedures wherein the retractor includes an external rail system which enables the surgeon to position a curved stabilization arm on either of the arms or the rack segment of the retractor and also includes a connector which releasably controls the rotation of the connector with respect to the retractor and the rotation of the stabilization arm with respect to the retractor as well as the rotational and sliding movement of a curved stabilization arm with respect to the connector upon actuation of a single knob or actuator.

19 Claims, 13 Drawing Sheets

U.S. PATENT DOCUMENTS

| | | | |
|---|---|---|---|
| 5,231,974 A | | 8/1993 | Giglio et al. |
| 5,242,240 A | | 9/1993 | Gorham |
| 5,290,300 A | | 3/1994 | Cosgrove et al. |
| 5,452,733 A | | 9/1995 | Sterman et al. |
| 5,503,617 A | | 4/1996 | Jako |
| 5,509,890 A | | 4/1996 | Kazama |
| 5,513,827 A | | 5/1996 | Michelson |
| 5,514,089 A | | 5/1996 | Walbrink et al. |
| 5,609,565 A | * | 3/1997 | Nakamura |
| 5,616,117 A | | 4/1997 | Dinkler et al. |
| 5,624,393 A | | 4/1997 | Diamond |
| 5,667,481 A | | 9/1997 | Villalta et al. |
| 5,727,569 A | | 3/1998 | Benetti et al. |
| 5,730,757 A | | 3/1998 | Benetti et al. |
| 5,749,892 A | | 5/1998 | Vierra et al. |
| 5,772,583 A | | 6/1998 | Wright et al. |
| 5,782,746 A | | 7/1998 | Wright |
| 5,807,243 A | | 9/1998 | Vierra et al. |
| 5,810,721 A | | 9/1998 | Mueller et al. |
| 5,836,311 A | | 11/1998 | Borst et al. |
| 5,846,193 A | | 12/1998 | Wright |
| 5,846,194 A | | 12/1998 | Wasson et al. |
| 5,857,965 A | | 1/1999 | Rootman et al. |
| 5,865,730 A | * | 2/1999 | Fox et al. ............... 600/229 |
| 5,875,782 A | | 3/1999 | Ferrari et al. |
| 5,888,247 A | | 3/1999 | Benetti |
| 5,894,843 A | | 4/1999 | Benetti et al. |
| 5,908,382 A | | 6/1999 | Koros et al. |
| 5,927,284 A | | 7/1999 | Borst et al. |
| 5,954,638 A | | 9/1999 | Spranza |
| 5,957,835 A | | 9/1999 | Anderson et al. |
| 5,967,973 A | | 10/1999 | Sherts et al. |
| 5,976,080 A | | 11/1999 | Farascioni |
| 5,984,864 A | | 11/1999 | Fox et al. |
| 5,984,867 A | | 11/1999 | Deckman et al. |
| 6,007,486 A | * | 12/1999 | Hunt et al. |
| 6,019,722 A | * | 1/2000 | Spence et al. |
| 6,036,641 A | * | 3/2000 | Taylor et al. ............ 600/232 |
| 6,102,854 A | * | 8/2000 | Cartier et al. |

FOREIGN PATENT DOCUMENTS

| | | |
|---|---|---|
| EP | 791 330 A2 | 8/1997 |
| EP | 0 808 606 | 11/1997 |
| EP | 820 721 A1 | 1/1998 |
| FR | 1019217 | 10/1952 |
| RU | 938967 | 7/1982 |
| WO | WO 95/17127 | 6/1995 |
| WO | 97/40738 | 11/1997 |
| WO | 97/40752 | 11/1997 |
| WO | WO 98/27869 | 7/1998 |
| WO | WO 98/48703 | 11/1998 |
| WO | WO 98/48704 | 11/1998 |

OTHER PUBLICATIONS

Angelini, G.D., A Simple, Inexpensive Method of Heart Retraction During Coronary Artery Bypass Surgery, Ann. Thoracic Surgery, vol. 46, pp. 246–247 (Aug./98).

Badellino, Michael M. et al., The Cardiac Rag, Simple Exposure of the Heart, Texas Heart Institute Journal, vol. 15, No. 2, pp. 134–135 (1988).

Chaux, Aurelio et al., A New Concept in St ernal Retraction: Applications for Internal Mammary Aratery Dissection and Valve Replacement Surgery, Ann. Thorac. Surg., vol. 42, pp. 473–474 (Oct./86).

Eguchi, Akiharu, Heart Retractor for Use in Anastomosis in Coronary Artery By–Pass Surgery, Japanese Journal of Thoracic Surgery, vol. 40, No. 1, pp. 1–2 (1987) (Translation Attached).

Matsuura, Akio, et al., A New Device for Exposing The Circumflex Coronary Artery, Ann. Thorac. Surg., vol. 59, pp. 1249–1250 (1995).

Parsonnet, Victor et al., Self–Retaining Epicardial Retractor for Aortocoronary Bypass Surgery, Journal of Thoracic and Cardiovascular Surgery, pp. 629–630 (date unknown).

Robicsek, Francis, Aortic Spoon–Jaw Clamp for Aorto–Saphenous Vein Anastomosis, J. Card. Surg., vol. 10, pp. 583–585 (1995).

Rousou, John A., Cardiac Retractor for Coronary Bypass Operations, Ann. Thorac. Surg., vol. 52, pp. 877–878 (1991).

Roux, D. et al., New Helper Instrument in Cardiac Surgery, Ann. Thorac. Surg., vol. 48, pp. 595–596 (1989).

DelRossi, A.J., et al., A New Retractor to Aid in Coronary Artery Surgery, The Annals of Thoracic Surgery, vol. 36, No. 1, pp. 101–102 (Jul./83).

Westaby, Stephen et al., Less Invasive Coronary Surgery: Consensus From the Oxford Meeting, Ann. Thorac. Surg., vol. 62, pp. 924–931 (1996).

* cited by examiner

CURVED STABILIZATION ARM FOR USE WITH SURGICAL RETRACTOR AND TISSUE STABILIZATION DEVICE AND METHODS RELATED THERETO

The present application is related to U.S. Pat. Ser. No. 60/117,333 filed on Jan. 24, 1999 and U.S. Pat. Ser. No. 091345,859 now U.S. Pat. No. 6,348,036 filed on Jul. 1, 1999 the priority thereof is claimed hereby and the disclosures thereof are incorporated herein by reference.

FIELD OF INVENTION

The present invention relates to surgical retractors and devices for stabilizing a predetermined area of the body during a surgical procedure, more particularly to surgical retractors and stabilizing devices used in connection with coronary artery bypass grafting surgical procedures, and more specifically to surgical retractors and stabilizing devices particularly configured for use with each other for such surgical procedures.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system leading to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, especially when multiple grafts are needed.

In the coronary artery bypass graft procedure, the surgeon may remove a portion a vein from another part of the body for grafting or detaches one end of a local artery and connects that end past the obstruction while leaving the other end attached to the existing arterial supply. When using a vein from another part of the body, the surgeon installs this portion at points that bypass the obstruction. In both cases, the objective is to restore normal blood flow to the heart.

In addition, when using this technique, the surgeon makes a long incision down the middle of the chest, saws through the sternum, spreads the two halves of the sternum apart. In the past, the surgeon then performed several procedures necessary to connect the surgical patient to a cardiopulmonary bypass machine to continue the circulation of oxygenated blood to the rest of the body while the heart is stopped and the graft is being sewn in place. Although such a procedure is one common technique, the procedure is lengthy, traumatic and can damage the heart, the central nervous system and the blood supply of the patient.

Interventional techniques, such as percutaneous transluminal angioplasty (PTCA) have gained popularity as the method of choice for therapy of atherosclerosis occlusions for several reasons. The transluminal approach is a less invasive technique that subjects the patient to fewer traumas and a shorter recovery time, especially when compared to bypass grafts, which utilize homologous tissue, such as saphenous vein grafts. Also, the patient often suffers complications at the donor site of the graft that may be worse than the sternotomy and anastomosis.

Although PTCA procedures are often successful, complications such as restenosis or thrombosis and embolism can occur. Restenosed vessels may often require surgical intervention for correction. The surgical correction of restenosis, like the conventional coronary bypass surgical procedure, required the heart to be stopped and the patient placed on a heart/lung bypass machine during the procedure.

In recent years, and in an effort to reduce expense, risk and trauma to the patient, physicians have turned to minimally invasive surgical approaches to the heart, such as intercostal and endoscopic access to the surgical site. With such procedures, the heart is beating during the surgical procedure. Thus, there is no need for any form of cardiopulmonary bypass and there is no need to perform the extensive surgical procedures necessary to connect the patient to such a bypass machine.

Over the years, there have been many attempts at performing minimally invasive bypass grafting on a beating heart. Until recently, these techniques have been thought of as being dangerous and difficult because of the delicate nature of the surgical procedure, the lack of adequate access through a reduced surgical field, and the lack of a way to adequately stabilize and reduce tissue movement at the graft site. These procedures are performed while the heart muscle is continuing to beat so that the heart continues to move in a three dimensional movement and the blood continues to flow while the surgeon attempts to evaluate the vessel and then sew the graft in place. Also, the surgical procedure to install the graft requires placing a series of sutures through the wall of an extremely small vessel and onto the artery and heart tissue that continuously moves during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 5,875,782 granted to Ferrari et al. and U.S. Pat. No. 5,894,843 granted to Benetti et al. an apparatus for stabilizing the predetermined area on a heart or other organ of a patient to enable a surgical procedure on a beating heart. The apparatus includes a bifurcated member having two elongated prongs and an elongated handle. The arm segment can be movably attached to a rib retractor so that a person is not required to hold the arm segment. In one disclosed embodiment, the apparatus further includes a device to hold the bifurcated member in a desired position against the surface of the heart so that a stabilizing force is applied against the heart.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the arm segment and the suction device may be locked into position against the surface of the heart It is therefore desirable to provide a new system and devices related thereto for stabilizing a predetermined area of the body, such as the heart and methods related thereto. It is particularly desirable to provide such a system and devices thereto that are less complex and more user friendly in comparison to prior art devices. Such systems and devices thereto preferably are simple in construction, versatile and are preferably low profile to minimize obstruction of the view of the surgeon or nurse to the surgical field.

SUMMARY OF THE INVENTION

The present invention features a system for retracting, stabilizing or manipulating a predetermined area of a body. The system includes a surgical retractor, a curved stabilization arm or apparatus and a tissue support or stabilization device, and methods of use related thereto. Also featured is a system that also supports any of a number of surgical implements, for example a diaphragm retractor, a valve retractor, a light or a suction device for use during a surgical procedure. The stabilization system and related devices and apparatuses thereto that are featured herein are particularly advantageous for use in performing off-pump coronary artery bypass grafting procedures in which the heart remains beating during the surgical procedure. One advantage of the present invention relates to the use of the curved stabilization arm to provide a low profile stabilization system so that obstruction of the physician's view of the surgical site is minimized. Another advantage of the present invention relates to the use of the external rail system on the arms of the retractor and even more preferably on the rack segment of the retractor. The use of the external rail systems allows the stabilization arm to be attached to the retractor at any desired location and does not require that the stabilization arm be slid on from an end of an arm or specially attached in certain specific locations. Additionally, the sled of the present invention allows for a full range of motion that is controlled by a single lever or knob that is easily manipulated by the surgeon.

The stabilization device preferably includes a device of the type commonly known as the Cohn Cardiac Stabilizer marketed by the Genzyme Corporation of Cambridge Mass., although horseshoe or suction type devices may also be used. The preferred form of the stabilization device is a generally square or rectangularly shaped member having a planar surface with centrally located opening therein. This opening is the area through which the surgeon performs the anastomosis or other procedure on the tissue of the beating heart. The stabilization device is preferably a two piece member so that once the anastomosis is completed, the pieces may be separated to remove the device from around the anastomosis. As described more fully below, flexible tapes are sutured through the tissue and then threaded through the stabilizing device. Once the stabilization device is positioned in the desired orientation and location in contact with the tissue, the flexible tapes are then pulled snug through the opening of the stabilization device to provide a system which minimizes the overall movement of the predetermined area of the tissue.

The stabilization arm of the present invention preferably includes a curved longated handle or shaft segment having a first end and a connector thereon for releasably connecting the stabilization device to the elongated handle first end. This connection allows the stabilization device to be pivotally and slidably moved to a desired position into contact with the predetermined area of the tissue of the patient while minimizing the interference of the stabilization device and stabilization arm with the field of view in the surgical field. The stabilization arm also includes amounting mechanism or sled member which is preferably slidable along the retractor arm segment for removably securing the stabilization arm to at least one of the rails on the retractor arms and/or the rack segment of the retractor. The stabilization arm may also be positioned above or below the horizontal pivot point of the sled member to farther increase the versatility of the stabilization system to allow the stabilization device to be positioned in the desired location in the surgical site.

According to one aspect of the present invention, the arms of the retractor are configured with a front edge and a step in the top surface thereof to form an elongated rail surface along substantially the entire length thereof. The step is preferably spaced apart a predetermined and consistent distance from the front edge and is also located on the interconnecting or rack segment of the retractor. Also, the stabilization arm preferably includes a mounting mechanism or sled member which is configured to removably engage the front edge and the step at any desired location on one or more of the arms or the rack segment of the retractor. The mounting mechanism includes a lever for selectively engaging the step and front edge on the arm or rack segment of the retractor so the mounting mechanism is removably and slidably secured to the arms or the rack segment.

In another aspect of the present invention, there is featured a surgical retractor including two arms, a rack segment and a plurality of sternal blades with at least one blade extending downwardly from each arm. Each blade includes an upper section adjacent to the bottom surface of the arm and a lower section extending distally from the arm. A slot on the bottom surface of the arms includes a tapered surface adjacent to the front edge thereof to facilitate the placement of the blades on the arms. A lip surface is also located adjacent to the slots on the bottom surface of the arms to securely retain the blades on the bottom surface of the arms during the procedure while still allowing the blades to be easily removable for initial positioning and subsequent sterilization following the procedure.

Each of the features described herein enable the user to determine the optimum position for the stabilization arm and stabilization device while ensuring that the surgeon's view of the surgical site is not unnecessarily obstructed. Additionally, these features allow the present invention to be used in many different medical procedures because of the versatility of system set up and orientation of the components of this invention.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein.

DESCRIPTION OF THE PREFERRED EMBODIMENT

Figure 1:
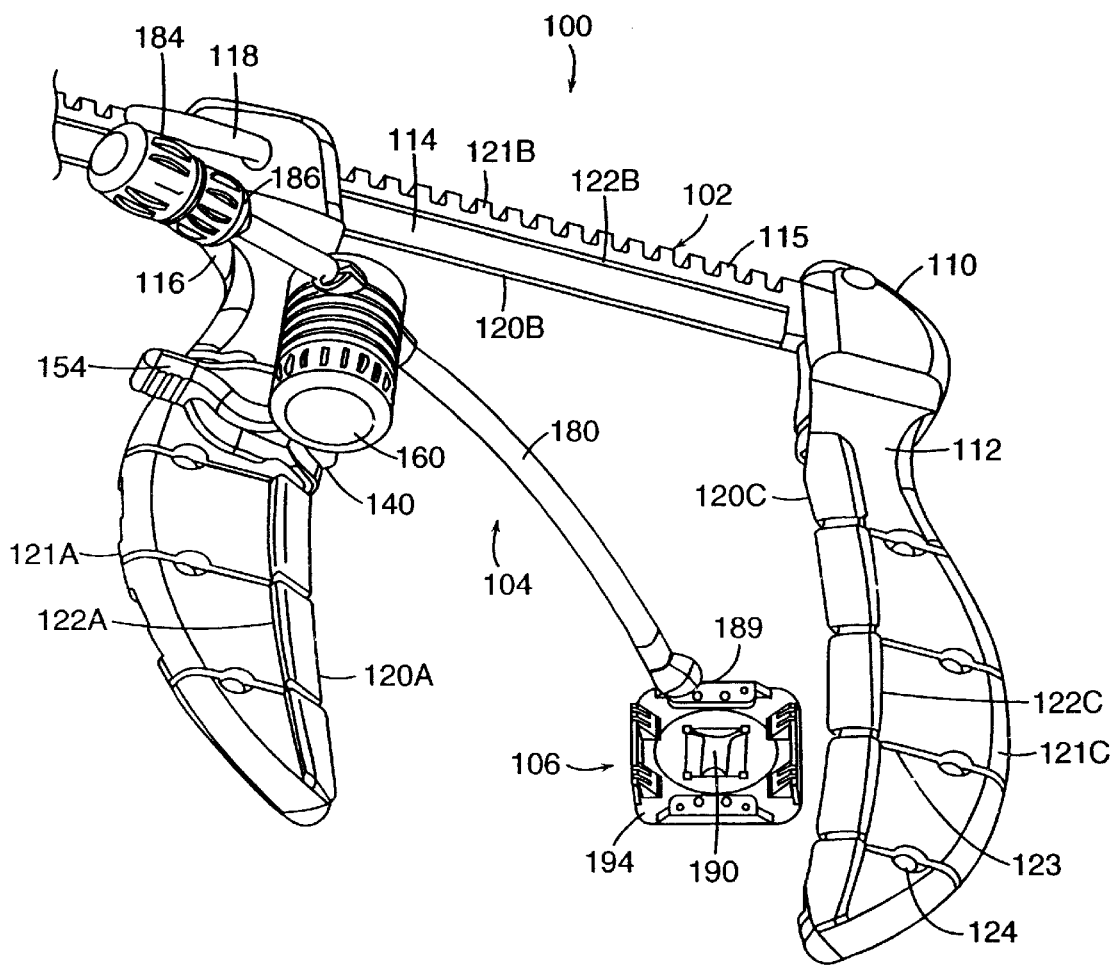
FIG. 1 is a perspective view of a stabilization system that assists in the stabilization of a predetermined area of a body according to a first aspect of the present invention.
Figure 2:
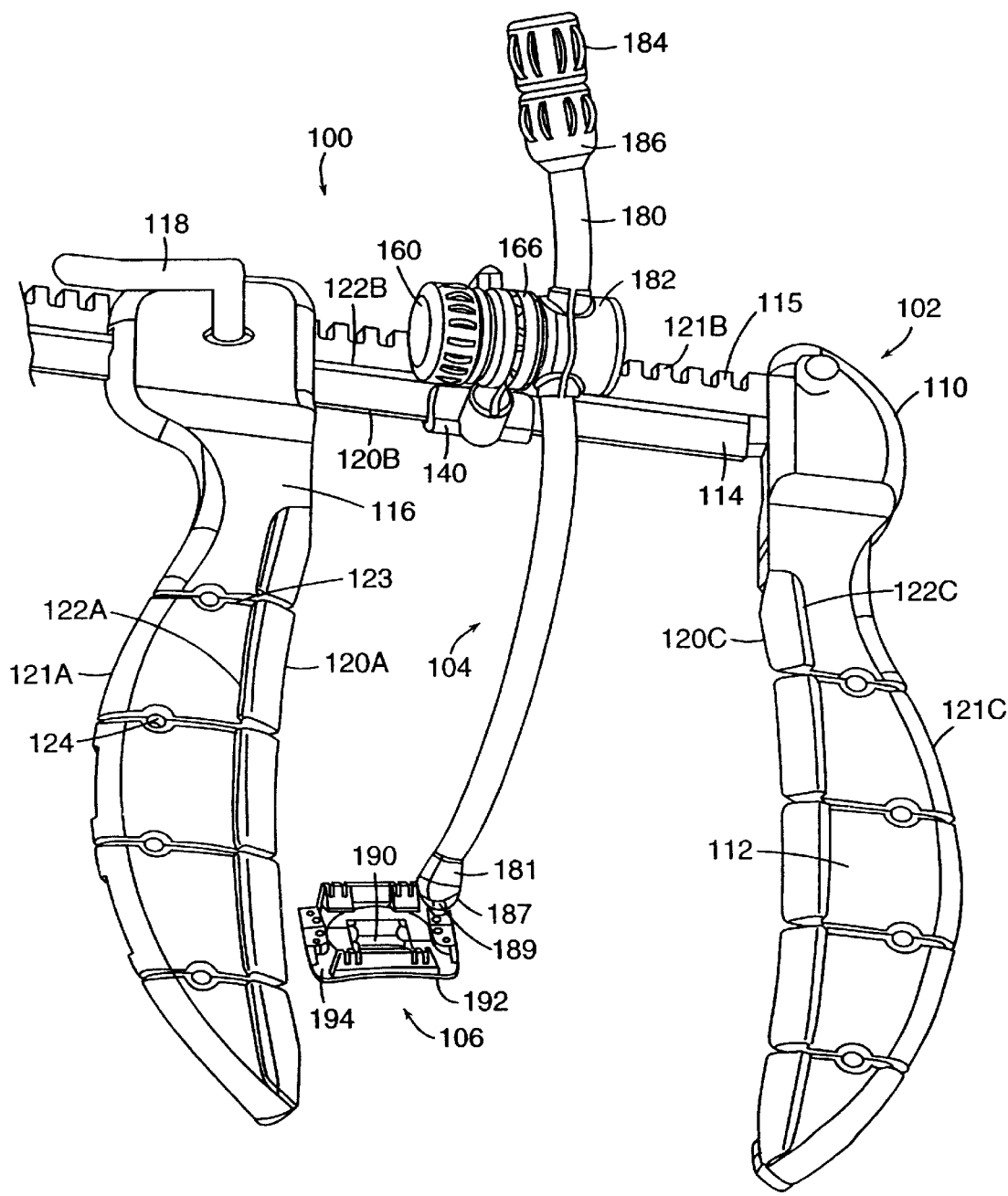
FIG. 2 is a perspective view of the stabilization system of the present invention wherein the sled member is positioned on a rack segment of the retractor.
Figure 3:
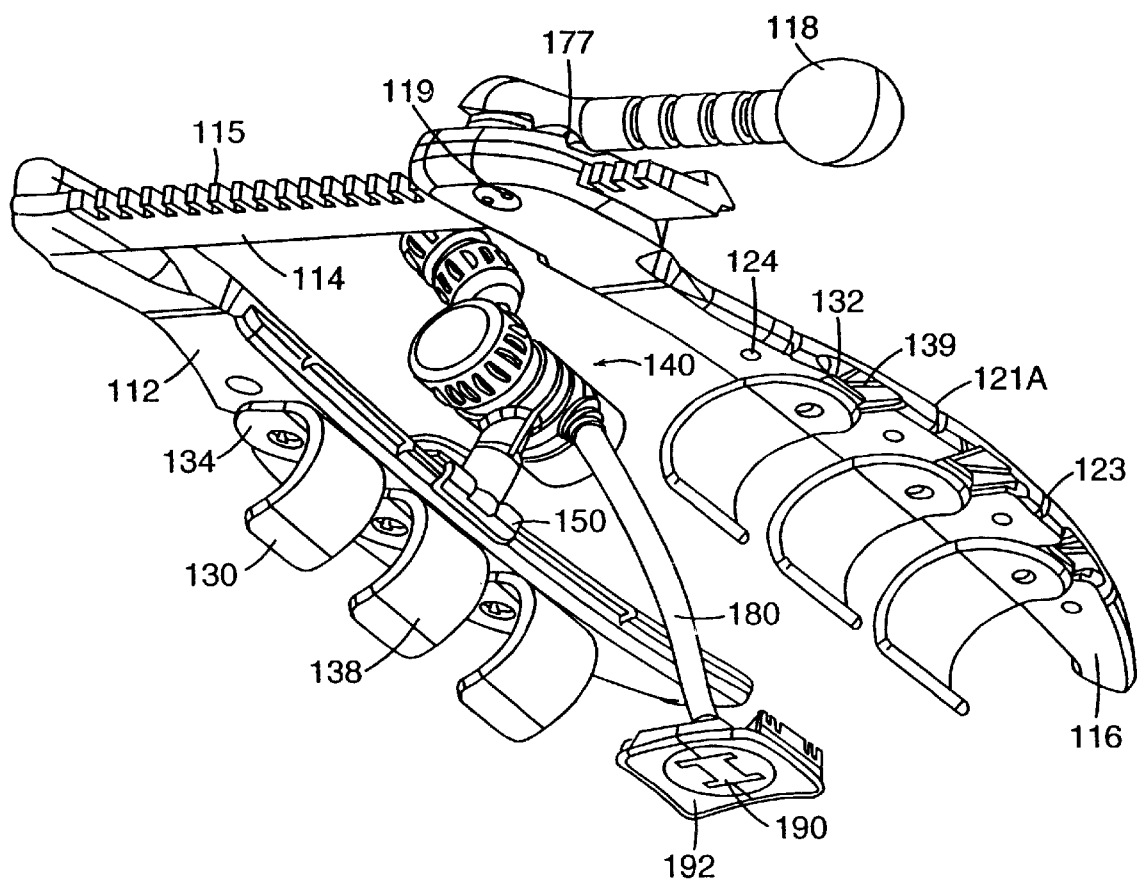
FIG. 3 is a bottom perspective view of the stabilization system of the present invention wherein the stabilization device is positioned beneath the arm of the retractor.
Figure 4A:
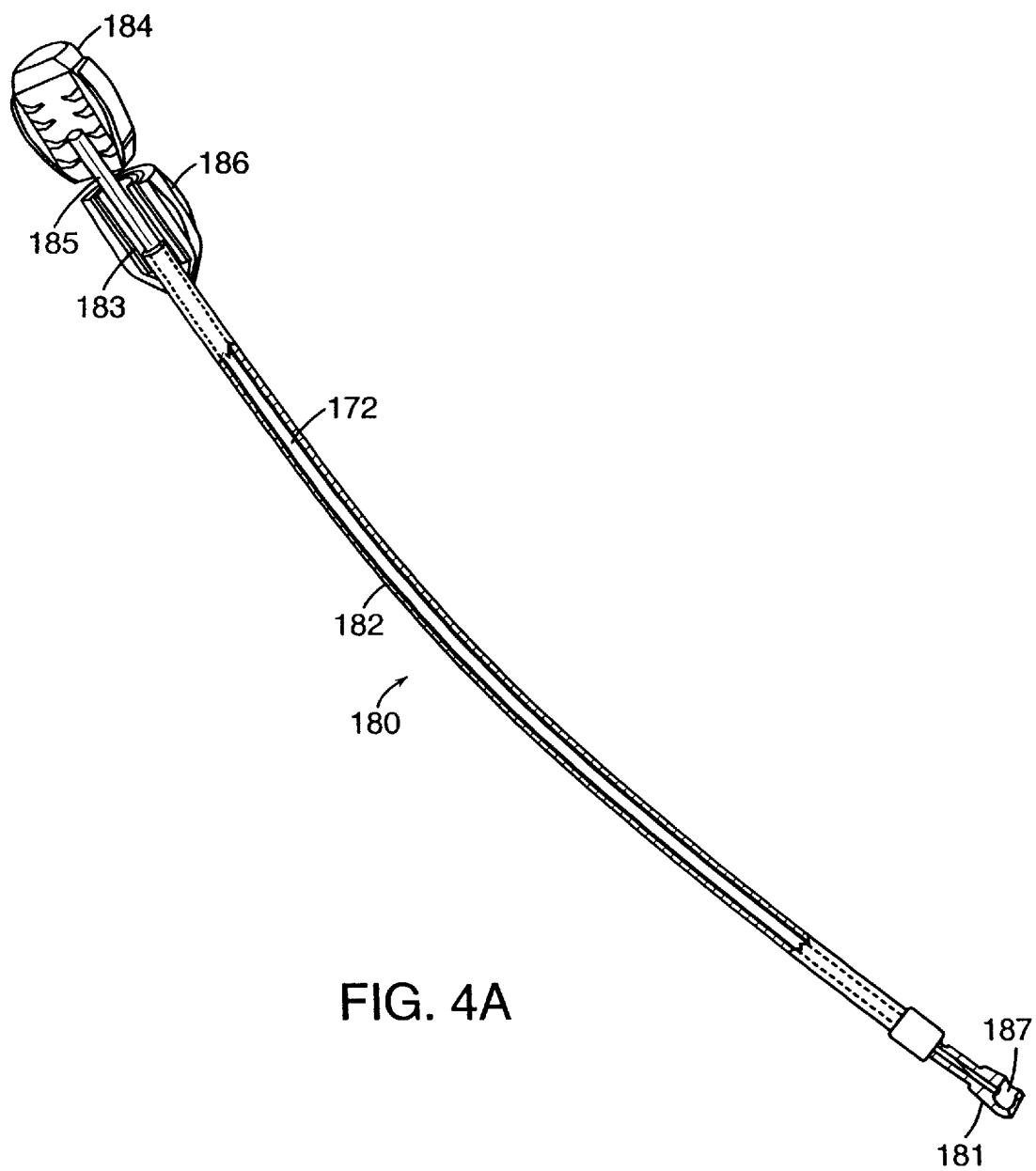
FIGS. 4A and 4B are cross sectional views of the stabilization arm of FIG. 1.
Figure 4B:
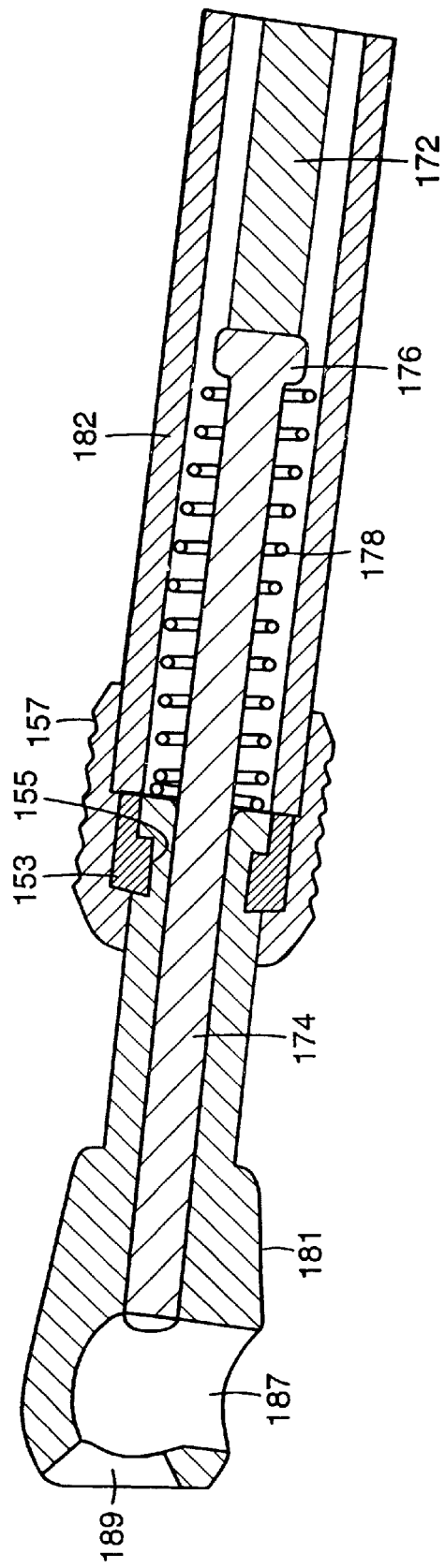
Figure 5A:
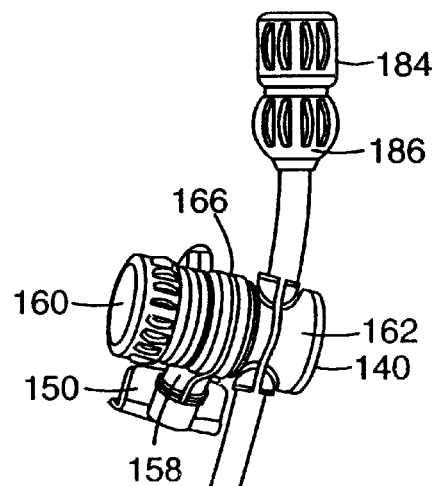
FIGS. 5A and 5B are various elevational views of the stabilization arm and stabilization device of the present invention.
Figure 5A:
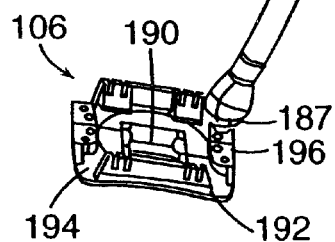
Figure 5B:
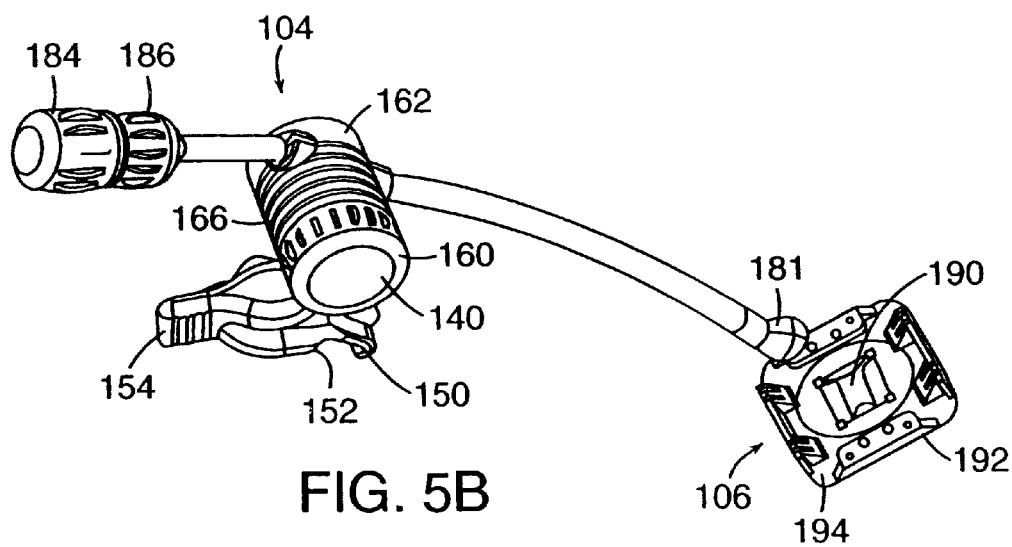
Figure 6:
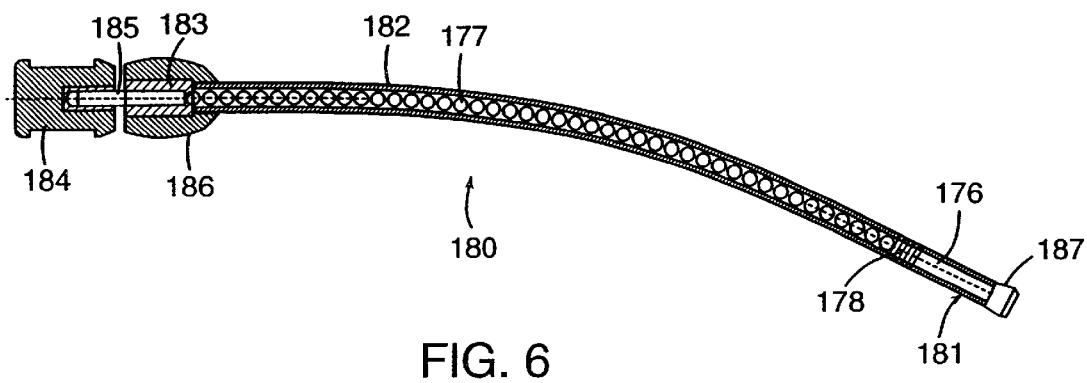
FIG. 6 is a cross section view of an alternate form of the stabilization arm of the present invention.

Referring now to the various figures of the drawings wherein like reference characters refer to like elements, there are shown various views of a preferred and alternate form of a stabilization system 100 according to the present invention. As described more fully below, the preferred embodiments of the present invention are intended for use in contributing to the accessibility or stabilization of a predetermined area of a body such as an area of a heart or other organ of a patient and to enable the physician to perform a surgical operation or procedure on a patient. The stabilization system 100 is particularly useful in connection with single or multiple vessel off-pump coronary artery bypass surgery on a beating heart through a sternotomy or ministernotomy incision although various other uses may be envisioned by a person skilled in this art.

A surgeon may use the stabilization system 100 to apply a slight contacting or compressive force on the heart in the area where the surgical procedure will occur so the heart's movement at that specific area is diminished. In a preferred form of this invention, the stabilization system 100 is used in combination with flexible tapes or sutures or other mechanical means so that the surface of the heart is stabilized using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is selectively restricted.

Systems for stabilizing the heart of a patient are particularly useful for various suturing techniques or procedures. One example of this type of procedure is the performance of an anastomosis for a bypass graft. In this type of procedure, the physician is attempting to suture the circumference of a blood vessel that may be about 1 mm to a moving blood vessel on the surface of the heart. Another area of use of the present invention may be in brain surgery, heart valve surgery or various types of blood vessel surgery where access and stability are critically important to avoid disastrous consequences or where it is desirable to have a precisely defined surgical field. One skilled in the art will appreciate that the present invention, although advantageously suited for heart surgery, can be used at any location on or within the body where tissue stabilization, retraction or isolation of a predetermined area is desired. This includes, but is not limited to, the liver, kidneys, bladder, stomach, intestines, brain and vascular and other soft tissue surgery. Additionally, one skilled in the art will appreciate, as hereinafter described, that the supporting components of the system can be adapted so that any surgical instrument or device can be self-supported during a surgical procedure.

Referring specifically to the drawings, the stabilization system 100 according to the present invention includes a retractor 102, a curved stabilization sub-system or stabilization arm 104 and a stabilization device 106. The retractor 102 is specifically configured so the stabilization arm 104 can be secured thereto. The retractor 102 preferably includes a rigid L-shaped member 110 having a first arm segment 112 and a rack segment 114. The retractor 102 also includes a movable second arm segment 116 having a handle 118 thereon which is movably associated with the L-shaped member 110.

The stabilization arm or sub-system 104 preferably includes a curved and elongate arm segment 180 that interconnects the retractor 102 and the stabilization device 106. The arm segment 180 preferably includes a first end having a distal connector 181 thereon to pivotally and removably retain the stabilization device 106 thereon. The arm segment 180 is attachable to the retractor 102 by a connector such as a mounting mechanism or sled member 140. The proximal end of the arm segment 180 preferably includes a movable knob 184 thereon that is rotatable with respect to the arm segment 180 to allow the movement of the stabilization device 106. The movable knob 184 allows the stabilization device 106 to be fixed, removable and/or pivotal with respect to the arm segment 180 by manipulating the movable knob 184 on the proximal end of the arm segment 180. This arrangement also allows the stabilization device 106 to be mountable on and removable from the distal connector 181 such that the stabilization device may be disposable while the stabilization arm may be disposable or reusable.

The preferred form of the stabilization device 106 is generally a rectangular shape having an opening or window area 190 therein. The stabilization device 106 preferably includes a first surface 192 that is generally planar and may include a textured surface thereon to facilitate the engagement between the stabilization device and the tissue of the heart or other predetermined area of the patient. The second surface 194 of the stabilization device 106 preferably includes a post member 196 extending upwardly therefrom. The post member 196 is preferably releasably and rotatably engaged by the distal connector 181 on the first end of the arm segment 180.

As described briefly above, the retractor 102 preferably includes a handle 118 located on the second arm segment 116 and the handle 118 is rotatable for displacing the two arm segments 112,116 with respect to each other. In the preferred embodiment, rotation of the handle 118 causes a pair of posts or pinions 119 to sequentially engage the teeth 115 located on the outer edge 121b of the rack segment 114 to increase or decrease the distance between the first and second arms 112 and 116. As shown, the handle includes a projection 177 on the bottom surface thereof and the projection fits in a slot located in the retractor adjacent to the arm and rack segment to allow the user to lock the handle into position once the arms are in the desired position. This feature is particularly useful where the retractor is reused for a relatively long period of time for multiple procedures because the pinions and teeth on the retractor will gradually wear due to the pressure from the chest of the patient. As the wear occurs, the pressure from the sternum may cause the arms to move towards each other unless the arms or handle are retained in a locked position. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth members 115 that engage the posts 119 or similar tooth engaging members located in operative contact with the handle 118 of the second arm segment 116. It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112. It is within the scope of the present invention, however, for the retractor 102 to be configured or designed with any of a number of means known to those skilled in the art for selectively displacing the first and second arm segments, 112 and 116 in a parallel, obtuse or acute angled manner.

At least one arm segment and preferably each arm segment, 112 and 116 respectively, and the rack segment 114 are configured so as to each have a front edge surface 120a, 120b and 120c extending along the inner surface of each element of the retractor 102 such that the front edges of each of the arms and the rack segment face each other. The retractor 102 also preferably includes an outer edge surface 121a, 121b and 121c extending along the outer surface of the first and second arms, 112 and 116 respectively, of the retractor 102. A step surface 122a, 122b and 122c extends along the top surface of the first and second arms, 112 and 116 respectively, and the rack segment 114 in a spaced apart relationship with respect to the front edges of each of the surfaces of the first and second arms and the rack segment to form an elongate lip or external rail surface on the arms and rack segment of the retractor. The step surface 122a–c is preferably located a preset distance back from the front edge and forms an acute angle facing away from the front edge thereof on each of the arms and the rack segment. As described hereinafter, the front edge surfaces 120a–c and the step surfaces 122a–c on the top surface of the arms and rack segment are particularly arranged and configured to face each other and so that the mounting mechanism or sled member 140 can be readily secured to the retractor 102 by engaging the front edge surface (120a, 120b or 120c) and the associated step surface (122a, 122b or 122c) on each of the first and second arms, 112 and 116, and the rack segment 114.

As also shown in the top views of the preferred form of the present invention, the front edge surfaces 120a and 120c of the first and second arm segments that are adjacent to the step surfaces 122a and 122c are of a preferably slightly concave orientation such that the mid point of the first and second arms are spaced apart from each other a greater distance than the distance of either or both of the inner or outer ends of the first and second arms, 112 and 116. Additionally, the outer edge surfaces 121a and 121c of each arm preferably has a greater curvature than the front edge surfaces 120a and 120c of the same arm so that as the retractor 102 spreads the chest of the patient, the motion of separating the first and second arms, 112 and 116, is emphasized to increase the amount the chest of the patient is spread. Therefore, at a given distance of separation between the first and second arms, 112 and 116, the midpoints of the outer surface of the arms will be separated a further distance than at the ends adjacent to the rack segment or at the ends farthest from the rack segment 114 due to the overall generally clam shell shaped configuration of the preferred form of the present invention. An advantage of this configuration is that the surgeon is provided with an opening in the sternum of the patient that is wider in the center than along the edges so that the most common area of work for the surgeon is larger than a conventional retractor for the same amount of separation.

Additionally, the top surface of each of the arms, 112 and 116, preferably include a plurality of slots 123 extending generally perpendicular to the lengthwise dimension of each arm. These slots 123 extend from the front edge surfaces 120a and 120c; through the step surfaces 122a and 122c; and to the outer edge surfaces 121a and 121c, respectively on each of the first and second arms, 112 and 116. These slots 123 are configured to extend through the front edge surface 120a and 120c of each arm, 112 and 116, to allow the sled member 140 to be moved therealong while not cutting or interfering with any sutures that may be positioned in the slots. Additionally, each of the slots 123 preferably include a through hole 124 in communication with the slot and extending through the arm. In the preferred use of the present invention, the slots 123 may be used to position sutures that have been threaded through the pericardium of the patient therein so that the pericardium or other tissue is retracted and held out of the line of sight of the surgeon by the sutures to better expose the desired surface of the heart. With the preferred form of the present invention, the sutures and clamps are retained out of the working area of the surgeon. The portion of the through hole 124 adjacent to the top and bottom surfaces of the arm are preferably tapered so that distal end of the clamps or other instruments that are used to hold the sutures may be placed and retained therein during the procedure. By allowing the distal ends of the instruments to be placed into the through holes 124, the sutures are held in a secure low profile position during the procedure and may be adjusted as needed at any time by lifting the instrument and then releasing the clamp and pulling the suture through the clamp and subsequently closing the clamp while it remains in the through hole or replaced therein. Additionally, it is anticipated that some surgeons may use these through holes to suture the retractor to the patient to minimize possible extraneous movement of the retractor during the procedure.

In an exemplary embodiment of the present invention, the bottom surface of each of the first and second arms, 112 and 116, on the retractor 102 include removable sternal blades 130 attached thereto. Each blade 130 is removable so as to facilitate the use of the retractor in a full or mini-sternotomy procedure by allowing for the selective positioning and spacing of the blades 130 as desired for the particular procedure as well as for the convenient resterilization of the retractor 102 and blades 130.

As illustrated, the blades 130 are positioned along the bottom surface of the arms 112 and 116 and are preferably pivotal in the horizontal and vertical directions with respect to the arms. The blades 130 are slidable into elongate ridged slots 132 on the bottom surface of the first and second arms, 112 and 116. The blades 130 may swivel a limited distance and are selectively positioned in the slots 132 so as to evenly distribute the retraction forces or pressure along the contour of the sternum of the patient. An upper section 134 of each blade 130 is particularly configured to facilitate the insertion of the blades into the retractor. In particular, the upper section 134 of the blade 130 is configured so that an upward extending and generally oblong shaped lip member is received in the ridged slots 132 located on the bottom surface of the first and second arms, 112 and 116. This surface further includes a raised ball member which slides in a further slot 139 located in the ridged slots. The ball member is slightly depressible so that it may be slid beyond the further slot 139 so that during the initial placement of the retractor, the blades may be positioned to extend nearly linearly along each arm in an insertion position. As the arms are retracted, the inner and outermost blades move to a retraction position to assume a slightly curved shape. In the preferred form of the present invention, the retraction position generally approximates the anatomy of the patient and allows the pressure of the sternum of the patient to be evenly distributed among the blades. The use of the ball member and the further slots and the ridged slots allow the blades to temporarily assume the linear configuration and also rise slightly with respect to the retractor to provide a lower profile and maintain the retraction edge. Once the blades are inserted into the sternum, the slight release of the pressure following the insertion allows the ball member to return to the innermost end of the farther slot and the blades may pivot slightly in the vertical and horizontal directions so that the blades follow the slightly curved shape of the retractor to provide optimum leverage to retract the sternum of the patient. The upper section 134 of the blade 130 extends generally along the bottom surface of the first and second arms, 112 and 116 and is positioned so the blade 130 extends a short distance inwardly of the front edge surfaces 120a and 120c of the arms 112 and 116. The blades 130 also include a lower section 138 which extends downwardly from the upper section 134 of the blade 130 in a curved manner to extend beneath the bottom surface of the retractor to readily engage the sternum of the patient. The lower section also preferably curves backward a short distance towards the outer edge surface 121 of the first and second arms, 112 and 116, to form a blade 130 having an overall C or L shape that facilitates the positioning and retention of the sternum of the patient adjacent thereto. Therefore, the blades 130 in conjunction with the displacement of the first and second arms result in the desired retraction of the tissue, bone etc. for the surgical procedure.

The stabilization sub-system or stabilization arm 104 of the present invention preferably includes an elongate arm segment 180 that interacts with the retractor 102 and the stabilization device 106. The arm segment 180 is attachable to the retractor 102 by a connector such as a mounting mechanism or sled member 140. The arm segment 180 preferably includes a hollow and rigid tubular member 182 that is curved at angle of less than about 30 degrees and more preferably about 26 degrees. This angle is chosen to provide the user with increased versatility in the placement of the stabilization device 106 in the desired location while also allowing the longitudinal sliding or movement of the arm segment with respect to the stabilization arm clamp as described in further detail below. The arm segment 180 includes a distal connector 181 on the distal end thereof to pivotally and removably retain post member 196 of the stabilization device 106 thereon. The proximal end of the arm segment 180 preferably includes a movable knob 184 and a fixed knob 186 thereon. The movable knob 184 includes a gripping surface thereon and a distally extending portion 185 which is threadedly connected to the proximal end of the arm segment 180. The distally extending portion 185 of the movable knob also includes an end surface thereon that contacts an elongate and movable member 172.

The movable member 172 is preferably a rigid member that extends from the proximal end of the arm segment 180, around the curve of the arm segment and to the distal connector 181 through the interior of the tubular member 182. The fixed knob 186 is fixed distally of the movable knob 184 and includes a threaded insert 183 therein to receive the distal extending portion 185 of the movable knob 184 therein. The fixed knob 186 on the tubular member 182 allows the user to rotate the stabilization device 106 and arm segment 180 by manipulating the fixed knob 186. Clockwise movement of the movable knob causes the movable member 172 to move distally within the threaded insert 183 of the arm segment 180 while counterclockwise movement of the movable knob causes the movable member 172 to move proximally within the threaded insert 183 of the arm segment 180 as described more fully below.

The distal connector 181 of this embodiment consists of a generally cylindrical member having an elongate slot 187 extending through at least one side thereof. Alternately, the distal connector may be bulbous or pear shaped member. In the preferred form of the present invention, the distal connector 181 is preferably fixed with respect to the arm segment 180 although it is contemplated that these components may also be movable with respect to each other. The distal connector 181 is retained on the distal end of the arm segment 180 by an outer sleeve 157 which extends between the distal end of the arm segment 180 and the proximal end of the distal connector 181. The outer sleeve also surrounds an inner connector 153 that engages a groove 155 in the proximal end portion of the distal connector and abuts the distal end of the arm segment to provide a limited amount of frictional resistance to the rotational movement of the distal connector 181 with respect to the arm segment 180. The slot 187 of the distal connector 181 is sized to allow the post member 196 of the stabilization device 106 to pass laterally therethrough to allow the stabilization device to be easily mounted on or removed from the stabilization arm 104 through the slot 187. As shown, the distal end of the distal connector includes a portion that is slightly larger than the rest of the slot surface to allow the post member 196 to be fully rotatable therethrough to increase the range of motion of the stabilization device. This arrangement preferably prevents the post member 196 of the stabilization device to pass distally from the slot 187 while increasing the range of motion and providing a centered position for the post member. This flexibility in positioning allows the surgeon to readily position the stabilization device 106 in the desired position and against nearly any surface of the heart of the patient.

Rotation of the movable knob 184 in a clockwise direction with respect to the arm segment and/or the fixed knob causes the distally extending portion 185 to move the movable member 172 distally in the tubular member 182. As the movable member 172 is moved distally in the tubular member 182, it contacts a pusher pin 174 located in the distal end portion of the arm segment. The pusher pin 174 preferably has a generally T-shaped cross section and includes a proximal lip 176 thereon. The proximal lip 176 contacts a spring member 178 which surrounds the distal portion of the pusher pin and which is retained between the proximal lip 176 and a lip formed by the proximal end of the distal connector 181. This distal movement of the pusher pin 174 with respect to the tubular member pushes the pusher pin 174 into the slot 187 of the distal connector 181 to press against the post member 196 of the stabilization device 106. The distal movement of the pusher pin 174 against the post member causes the post member 196 to press against the lower lip surfaces on the distal surface of the slot 187 of the distal connector 181 to preferably fixedly retain the post member therein and prevent further movement of the stabilization device. The distal movement of the pusher pin 174 also prevents rotation of the distal connector relative to the arm segment by increasing the frictional resistance between the inner connector 153 and groove 155.

Rotation of the movable knob 184 in a counterclockwise direction with respect to the arm segment and/or the fixed knob causes the distally extending member 185 to move proximally in the threaded insert 183 of the tubular member 182. As this occurs, the spring member 178 pushes against the lip of the pusher pin 174 and causes the distal end of the pusher pin 174 to move proximally away from the slot 187. This proximal movement of the distal end of the pusher pin 174 allows for the rotation and/or release of the post member 196 of the stabilization device from the distal connector 181.

The generally cylindrical shape of the distal connector 181 and the opening in the slot 187 optimize the connection between the distal connector 181 of the handle and the post member 196 of the stabilization device. This arrangement enables the post member to be selectively retained within the distal connector 181 while allowing pivotal and rotational movement therebetween. Additionally, the rotation of the distal connector with respect to the arm segment and the use of the movable member 172 and spring member 178 provide for an increased versatility in the use of the curved tubular member in the present invention. This increased versatility allows the user to further manipulate the handle member and stabilization device to the desired location in the surgical field. This freedom of movement and versatility is desirable for the present invention where space is at a premium and the device must be as versatile as possible to accommodate the surgeons needs without undue experimentation.

In an alternate embodiment of the present invention, the movable knob 184 includes a gripping surface thereon and is threadedly connected to a threaded insert 183 on the proximal end of the arm segment 180. The arm segment 180 preferably includes a hollow and rigid tubular member 182 having a plurality of ball members 177 therein and that is curved at an acute angle which is preferably less than about 30 degrees and even more preferably about 26 degrees. The arm segment 180 includes the distal connector 181 on the distal end thereof to pivotally and removably retain post member 196 of the stabilization device 106 thereon. The proximal end of the arm segment 180 preferably includes the movable knob 184 and a fixed knob 186 thereon. The movable knob 184 includes a gripping surface thereon and the distally extending portion 185 which is threadedly connected to the proximal end of the arm segment 180. The distally extending portion 185 of the movable knob also includes an inner surface thereon that contacts a plurality of ball members 177. The ball members 177 are preferably loosely positioned in the tubular member 182 and extend from the proximal end of the arm segment 180, around the curve of the arm segment and to the distal connector 181 through the interior of the tubular member 182. Alternately, the ball members 177 may include an elongate wire or thread member (not shown) extending therethrough to ensure that the individual ball members do not separate and fall into the chest cavity of the patient in the event of a catastrophic failure of the arm segment. The movable knob also includes an inner surface thereon that contacts the plurality of ball members 177. The ball members 177 preferably extend from the proximal end of the arm segment 180, around the curve of the arm segment and to the distal connector 181 through the interior of the tubular member 182.

The fixed knob 186 is fixed distally of the movable knob 184 on the tubular member 182 of this embodiment to allow the user to rotate the stabilization device 106 and arm segment 180 by manipulating the fixed knob 186. The movable knob 184 is preferably threadable into the proximal end of the fixed knob 186. Clockwise movement of the movable knob causes the ball members 177 to move distally within the arm segment 180 to press the pin member 176 against the post member 196 in the slot 187. Counterclockwise movement of the movable knob allows spring member 178 to expand and cause the ball members 177 to move proximally within the tubular member 182 of the arm segment 180. Expansion of the spring member 178 also causes the distal end of the pin member 176 to move from the slot 187 to allow pivoting and/or the release the post member of the stabilization device 106 from the slot.

The stabilization arm 104 of the preferred embodiment also includes a sled member 140 operatively connected thereto. The sled member 140 is configured so the surgeon has multiple axis positioning capability for the stabilization device 106 while requiring a minimum of manipulation. The sled member allows movement along a horizontal axis and movement along a vertical axis in response to rotation of a single knob 160 as described more fully below. In an exemplary embodiment, the bottom section of the sled member 140 includes a front edge lip 150, a movable second lip 152 and an actuator lever 154. The actuator lever 154 is pivotally connected to an elongate slot in the second lip 152 by a pin 158 which is preferably offset with respect to the axis of rotation of the actuator lever 154 so that movement of the actuator lever 154 causes the second lip 152 to move towards and away from the front edge lip 150. The front edge lip 150 is configured so that the interior of this lip conforms generally to the shape and configuration of any of the front edge surfaces 120*a–c* of the retractor. The front edge lip 150 also includes a portion that extends backwards under the front edge surfaces 120*a–c* of the arms and/or rack segment of the retractor so the front edge lip 150 preferably forms an acutely angled surface that is easily secured at any location on any of the front edge surfaces 120*a*, 120*b* or 120*c* of the retractor 102.

As also shown in the drawings, the second lip 152 of the sled member 140 is a semicircular or oblong shaped member that is disposed in the bottom of the sled member 140 a distance back from the front edge lip to selectively engage the recessed side of any of the step surfaces 122*a–c* of the retractor. The second lip 152 also is generally configured so the inside interior surface 151 of the sled member 140 extends arcuately across and lies upon the top surface of the retractor 102 between a front edge surface 120*a–c* and the associated step surface 122*a–c* of the retractor. The second lip 152 is slidably mounted on the bottom side of the sled member 140 and is movable in response to rotation of the actuator lever 154 to form an acute step surface engaging angle between the sled second lip 152 and the inside interior surface 151 to securely retain the selected step surface 120*a*, 120*b* or 120*c* therein.

In the preferred embodiment of the present invention, the sled member 140 also includes an upper section including a lever or knob 160, a stabilization arm clamp 162, a sled pin clamp 166, and a threaded rod 170 therein. This portion of the sled member 140 provides the surgeon with the rotational movement of the stabilization arm 104 in a combination of horizontal and vertical directions as well as allowing for the sliding and rotational movement of the arm segment 180 therethrough, all of which are advantageously controlled by the operation of the single lever or knob 160 that is located along the periphery of the operative field. Furthermore, the arc of curvature of the arm segment may be oriented up or down and the arm segment may also be positioned above or below the horizontal axis of the knob 160 on the upper section to provide the surgeon with further options to minimize the interference of the stabilization arm with access to the surgical site.

The sled pin 158 extends upwardly from the portion of the bottom section of the sled member 140 to form a first or vertical axis of rotation between the bottom section that includes the front edge lip 150, second lip 152 and the actuator lever 154 described above and the upper section described below. This arrangement enables the bottom section of the sled member to be rotatable with respect to the upper section of the sled member 140 independently of whether or not the sled member is locked into position along the arms and/or rack segment of the retractor. Additionally, this orientation allows the upper section of the sled member to be preferably positioned directly above the front edge of the retractor as shown. This orientation significantly increases the range of motion of the sled member and therefore the range of motion of the stabilization arm and ultimately significantly increases the versatility and range of motion of the stabilization device. For example, rotation of the sled member 140 and rotation of the stabilization arm 104 will allow the user to position the stabilization device 106 beneath the arms and/or rack segment by allowing the aperture 164 which contains the arm segment 164 to extend inwardly of the front edge 120 of the retractor 102 and the sled pin 158.

These features are additionally enhanced by the use of the curved arm segment 180 to allow the user to position the stabilization device in a wide variety of positions including under the arms of the retractor while ensuring that the proximal portion of the arm segment is only minimally positioned in or upstanding from the surgical field. This ability to select a wide variety of orientations is particularly useful in situations where the posterior surface of the heart is being operated on as well as in certain situations where the selected portion of the heart is manipulated to a side of the operative field. Additionally, with the curved arm segment, the radius of curvature may be oriented upwardly or downwardly to provide the user with yet another option to locate the optimum position of the stabilization device. For example, when the arm segment is oriented so the arc of the curvature of the arm segment faces downwardly, the distal end of the arm segment assumes a low profile to ensure that the arm segment does not interfere with the operation. This is particularly true when the arm segment is oriented below the horizontal axis of the knob 160. Similarly, when the arc of curvature faces upwardly, the surgeon may approach the surgical field at a sharper angle than with other stabilization systems and this orientation may be further emphasized by orienting the arm segment above the horizontal axis of the upper section of the sled member.

Figure 7:
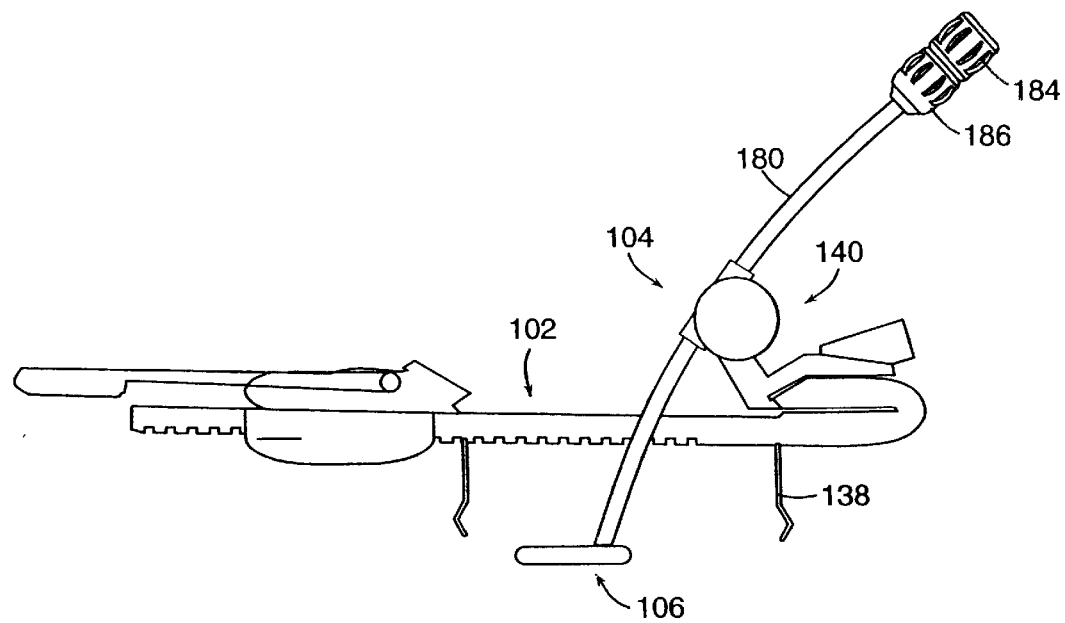
FIG. 7 is a side view of an alternate form of the stabilization system shown on a side view of the retractor.

Furthermore, the sled pin may also be angled to cause the upper section of the sled member to extend inwardly of the front edges of the arms and rack segment to further increase the versatility of the present invention as shown in FIG. 7. This type of orientation may require the arm segment to be oriented at an angle that is generally greater than perpendicular to the width dimension of the arms or rack segment. The sled pin 158 may be rotatably received in a recess or pocket 168 that is formed between left and right sections of the sled pin clamp 166 on the sled member 140. In this way, and as described hereinafter, the upper section of the sled member 140 can be rotated by the surgeon about the sled pin 158 to facilitate the horizontal and rotational positioning of the stabilization arm 104 and stabilization device 106 at the desired predetermnined area on the heart of the patient.

The left and right sections of the stabilization arm clamp 162 on the sled member 140 are configured so as to form a through aperture 164 therein. This aperture 164 is preferably offset from the rotational or horizontal axis of the knob 160 and threaded rod 170 to allow the arm segment to be positioned above or below to increase or decrease the angle of approach of the arm segment 180 to the operative field. As shown, a preferred configuration orients the aperture 164 above the horizontal axis H of the knob 160. As described herein, the horizontal axis H extends generally along the threaded rod 170. If desired by the surgeon, the aperture 164 and therefore the arm segment 180 may be positioned below the horizontal axis of the knob so that the arm segment will approach the operative field at a lower angle. The aperture 164 slidably and rotationally receives the arm segment 180 of the stabilization arm 104 therein. The stabilization arm clamp 162 is rotatably disposed about the threaded rod 170 to allow the arm segment to be rotatable about the longitudinal axis of the threaded rod 170 as well as being separately rotatable and slidable with respect to the aperture 164. The rotational surfaces between the stabilization arm clamp 162 and the sled pin clamp 166 may also preferably have a plurality of complementary ridges and valleys thereon so as to form a poker chip type surface on each of these surfaces of the clamps. The use of this type of roughened surface preferably limits the rotational movement of the stabilization arm clamp 162 with respect to the sled pin clamp 166 when the knob 160 and threaded rod 170 are intermediately or fully tightened by providing an additional source of friction that must be overcome to rotate the arm segment with respect to the stabilization arm clamp 162. Additionally, the use of this type of surface facilitates the fine positioning of the stabilization device 106 by preventing the rotational movement of the stabilization arm clamp 162 while the surgeon is still able to overcome the frictional resistance to the rotational and sliding movement the arm segment 180 when the knob 160 is not fully tightened.

The preferred form of the present invention also includes the threaded rod 170 that is fixedly attached to the knob 160 and extends between the knob 160 and the outer section 167 of the sled pin clamp 166. In this way, and as described hereinafter, the stabilization arm clamp 162 and thus the arm segment 180 of the stabilization arm 104 can be rotated by the surgeon about the threaded rod 170 prior to the knob 160 being rotated to a fully engaged position wherein relative movement is prevented. Additionally, the arm segment 180 may also slide and/or be rotated with respect to the stabilization arm clamp 162 through the aperture 164 to facilitate positioning of the stabilization device 106 through the manipulation of an actuation member such as the single knob described herein or through a single lever or handle.

The knob 160 is secured to one end of the threaded rod 170 and the other end of the rod engages the outer section 167 of the sled pin clamp 166. The sled pin clamp 166 and the stabilization arm clamp 162 are each located rotationally about the threaded rod 170 and are compressively controlled thereby. Thus, rotation of the knob 160 in one direction (e.g., clockwise direction) moves the left and right sections of each of these clamps towards each other (i.e., compresses the clamps) so as to clamp onto each of the sled pin 158 and the arm segment 180 respectively. The compression of the sled pin 158 by the sled pin clamp 166 limits the rotational movement of the bottom section of the sled member 140 with respect to the upper section of the sled member 140 to limit the generally horizontal movement of the stabilization arm 104 with respect to the retractor 102. The compression of the arm segment 180 by the stabilization clamp 162 prevents the rotational and sliding movement of the arm segment 180 through the aperture 164 and therefore causes the stabilization device 106 to be held in a fixed position relative to the sled member 140 and the retractor 102 to limit the generally vertical movement of the stabilization arm 104 with respect to the retractor 102. Rotation of the knob in the opposite direction (e.g., counterclockwise direction) causes each of these clamps 162 and 166 to separate and enable the clamps to be rotatable about the sled pin 158 and/or the threaded rod 170. In the preferred form of the present invention, each of the clamps include a spring member (not shown) therein to facilitate the separation of the clamps as the knob is rotated counterclockwise. Additionally, the arm segment 180 can slide and rotate within the stabilizer arm clamp 162 and through the aperture 164.

As one skilled in the art will appreciate, the knob 160 can be rotated in the direction of clamping so as to increase the resistance of rotation about the sled pin 158 and to increase the resistance to sliding and/or rotation of the arm segment 180 in the aperture, without completely preventing such rotation and/or sliding. This may be done to facilitate the precise positioning of the stabilization device 106 by the surgeon. Additionally, the clamps 162 and 166 may be arranged so that the initial rotation of the movable knob 184 may first release either the sled pin 158 or the arm segment 180 prior to the release of the other of the sled pin 158 or arm segment 180. Additionally, the clamps 162 and 166 may be arranged to initially allow for or prevent the rotation of the stabilization arm clamp 162 relative to the sled pin clamp 166. Thereafter, the clamps 162 or 166 may release the sled pin 158 and arm segment 180 at the same time or sequentially. Although the preferred form of the present invention is described herein as a knob, it is anticipated that a lever or similar actuation member may be used to accomplish the desired, orientation of the stabilization device 106 relative to the retractor 102.

The use of the stabilization system 100 according to the preferred aspect of the present invention can be best understood from the following discussion with reference to the drawings. Although the following discussion makes reference to the use of the stabilization system specifically in connection with a coronary artery bypass grafting surgical procedure, the use of the stabilization system of the present invention is not limited to such uses.

After appropriately preparing and positioning the patient for the surgical procedure and completing those actions required in advance of the use of the stabilization system, the arms 112 and 116 of the retractor 102 would be closed such that the upper portion 134 of the blades 130 are generally abutting each other. The surgeon then positions the lower sections 138 of each of the blades adjacent to the incision and pushes down on the retractor or otherwise manipulates the blades and the patient so the blades are pushed through the incision and past the sternum.

After inserting the retractor, the surgeon displaces the two retractor arm segments 112,116 with respect to each other by rotating the handle 118 on the second arm segment 116. As the surgeon opens the sternum of the patient, they also release any underlying connective tissue and open the pericardium surrounding the heart of the patient. In order to provide for visualization of the heart, the pericardium that surrounds the heart is retracted by placing sutures (not shown) through the pericardium and then threading the sutures through the slots 123 on the retractor arms to ensure that the sutures are spaced apart from the operative field. As mentioned above, the clamps (not shown) holding the sutures may then be positioned in the slots so that the distal end of the clamping instrument is positioned in the through holes 124. This allows the sutures and clamps to be positioned out of the way of the surgeon for the subsequent procedure. After performing any subsequent actions to further open the sternum of the patient to create the desired field of view and assess the viability of the heart to perform the bypass grafting procedure on one or more vessels, the surgeon mounts the stabilization arm 104 onto one of the retractor arm segments 112,116 or the rack segment 114 in the position that they anticipate will provide the best access while minimizing the obstruction of their view for the particular procedure.

It should be recognized that the bypass grafting procedure may involve the arteries or branches thereof on nearly any surface of the heart including the posterior or backside of the heart. Therefore, having the capability to mount the stabilization arm to the rack segment 114 or either of the arms, 112 or 116, of the retractor can be particularly advantageous. With the preferred form of the present invention, the stabilization arm 104 may also be positioned with the arc of curvature up or down and the stabilization arm 104 may be positioned above or below the horizontal axis of the sled member. Additionally, the aperture on the sled member that contains the arm segment may be positioned inwardly or outwardly of the inner edge of the arms or rack segment of the retractor and the distal connector may be rotated relative to the arm segment as desired by the surgeon. The retractor 102 is typically arranged on the body so the throat of the retractor faces the head of the patient and the surgeon is typically located on one side of the patient while a nurse is located on the other side of the patient and instruments are passed across the body of the patient throughout the procedure. Therefore, with the preferred form of the present invention, the surgeon has an additional surface to choose from when they are deciding which surface will provide the best access to the desired surface of the heart while not interfering with the procedure.

To mount the stabilization arm 104 onto the retractor 102, the surgeon rotates the sled actuator lever 154 so the second lip 152 is in a disengaged position and is spaced from the front edge lip 150 of the sled member 140. After so configuring the sled member 140, the surgeon positions the sled member 140 on the retractor 102 at any of a number of available positions on the arms, 112 and 116, or the rack segment 114 by positioning the front edge lip 150 over the front edge of the selected arm or rack segment. With the preferred configuration of the sled member 140, the surgeon need not slide the sled member along the entire length of a retractor arm or be required to select from a limited number of predetermined positions, but can place the sled member 140 directly at the desired position. In this way, a surgeon can removably position the sled member 140 anywhere on the rack segment 114 or the arms 112, 116 of the retractor 102 without having to first assemble the retractor with a sled member 140 initially positioned in any of these predefined areas. An advantage of this configuration is that the surgeon may initially position the sled member 140 in a position that they anticipate will be close to where they will ultimately want it. If during the procedure, a different location is needed or provides better access, the surgeon may either slide the sled member 140 along the previously selected arm or rack segment to the desired location or they may remove the sled member 140 from the retractor and try various locations to see which location on the arms and rack segment provides the best access for the particular procedure. In addition, such a sled configuration also allows the surgeon to perform certain surgical procedures without having to worry about the sled member 140 cutting or interfering with any sutures that may be passing over the retractor while positioning the sled member 140. Furthermore, if multiple blood vessels are operated on or access to multiple surfaces is desired, the orientation of the sled member may be readily adjusted to accommodate the needs of the particular part of the procedure.

The surgeon may next fix the sled member in place by positioning the front edge lip 150 of the sled member 140 over the front edge surface 120a, 120b or 120c on the desired area of the retractor 102 and then rotating the sled actuator lever 154 partially or fully, as desired, so the second lip 152 contacts and engages the vertical extending surface of the corresponding step surface 122a–c on the retractor 102. Once the surgeon has placed the sled member on the retractor, they may then initially position the stabilization device 106 near the ultimate desired location along the surface of the heart by loosening the movable knob 184 and rotating the fixed knob 186 as well as loosening the knob 160 on the sled member to orient the stabilization device 106 and stabilization arm 104 in the tentative desired position. It should be recognized that this process may include orienting the arc of curvature of the arm segment up or down and may be repeated as often and whenever necessary to modify the position of the stabilization device 106 at the desired location or area of the heart.

Thereafter, the surgeon may loosen knob 160 and rotate the top section of the sled member 140 about the sled pin 158 and also move the arm segment 180 lengthwise and/or rotationally with respect to the sled member 140 to position the arm segment within the stabilization arm 162 clamp through aperture 164 so as to position the stabilization device 106 with respect to the predetermined area of the heart to be stabilized. Once the surgeon is satisfied with the location of the stabilization device 106 on the heart of the patient, the surgeon may tighten knobs 160 and 184 to ensure that the stabilization arm 104 and stabilization device 106 are retained in the desired position throughout the remainder of the procedure. Once the stabilization device 106 is in the desired contacting relationship with the predetermined area of the heart, the surgeon may tighten the knob 160 of the stabilization arm 140 so as to prevent further rotation about the threaded rod and the sled pin and also to prevent sliding of the arm segment in the aperture. The surgeon may also tighten the knob 184 of the arm segment 180 so as to tighten the connection between the distal connector 181 on the arm segment and the post member 196 on the stabilization device 106 prevent further motion of the stabilization device 106 about the end of the stabilization arm 104.

After completing the grafting procedure, the surgeon may then remove the stabilization arm 104 and stabilization device 106 by essentially reversing the above described steps or the surgeon may simply release the actuator lever 154 and remove the entire stabilization arm and stabilization device from the operative field. Similarly, the actuator lever may be moved to a position between the engaged and disengaged positions so that the stabilization arm may be moved out of the way while a subsequent procedure is performed or to attach a new stabilization device thereon.

Figure 8A:
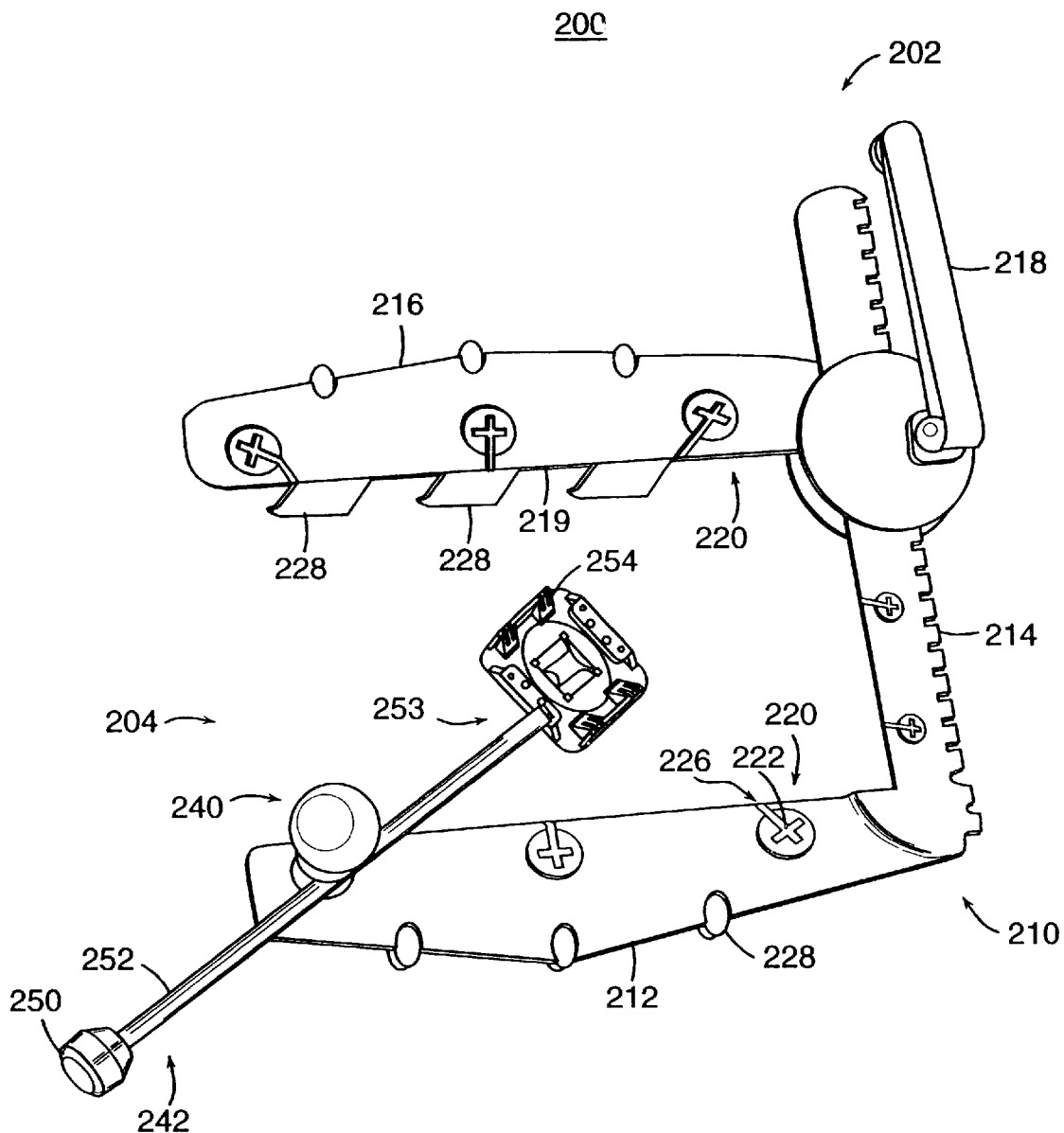
FIGS. 8A, 8B, and 8C are various elevational views of an alternative embodiment of the present invention.
Figure 8B:
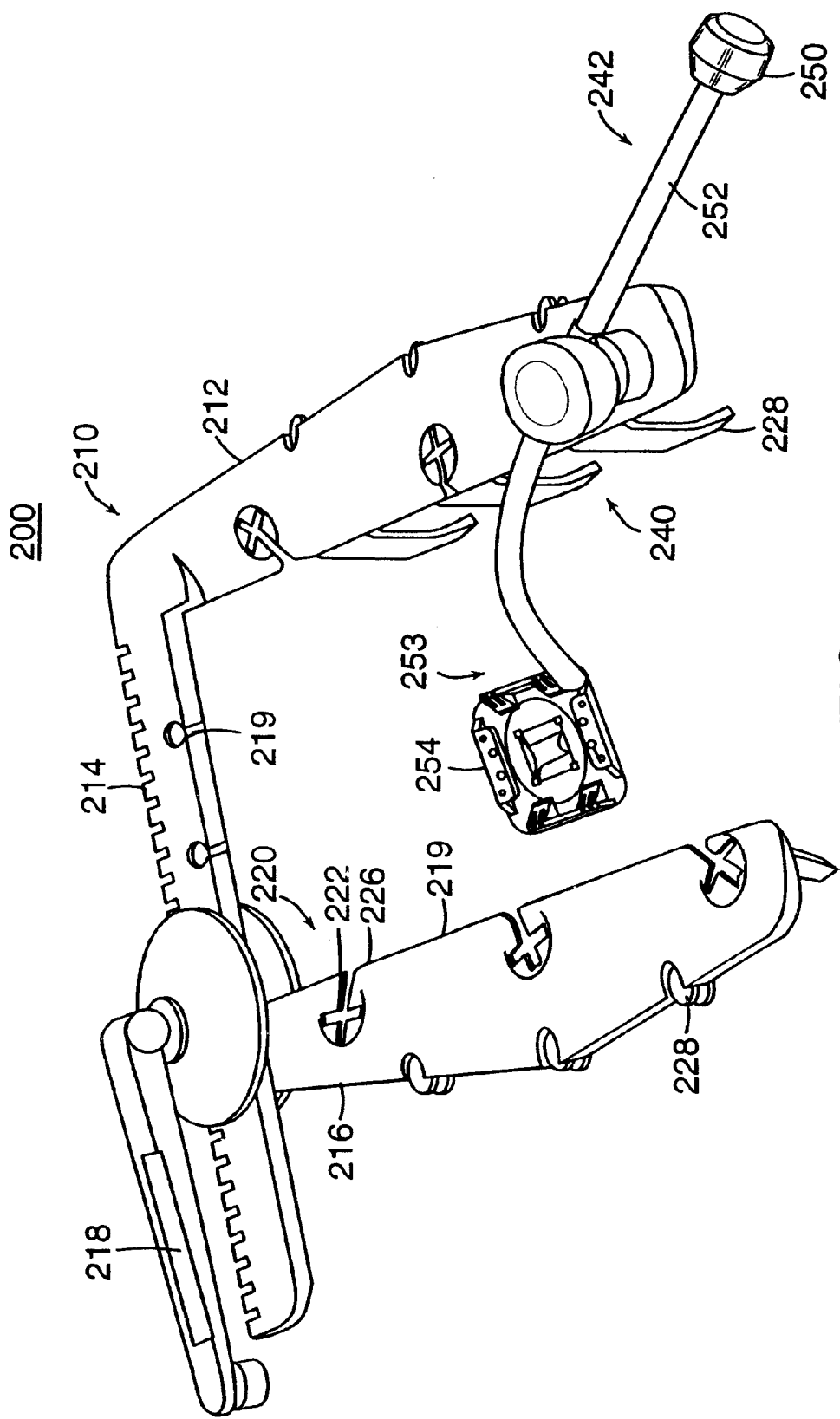
Figure 8C:
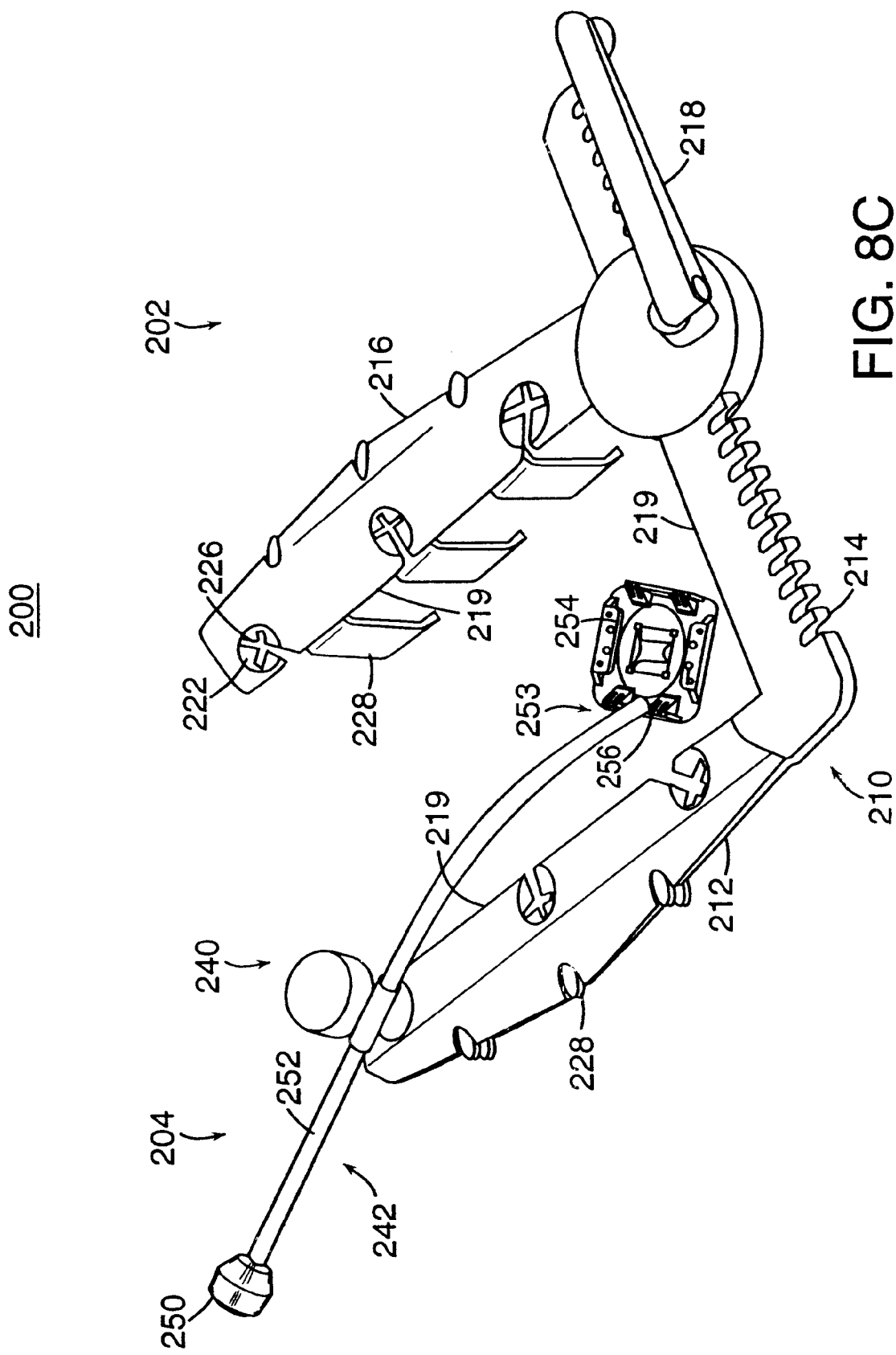

Referring now to FIGS. 8A–B, there is shown various perspective views of a stabilization system 200 according to a further embodiment of the present invention for stabilizing a predetermined area of a body such as a predetermined area of a heart or other organ of a patient to enable the conduct of a surgical operation/procedure. The stabilization system 200 includes a retractor 202 and a stabilization sub-system or stabilization arm 204, where the retractor is specifically configured so the stabilization sub-system can be secured thereto.

In an exemplary embodiment, the retractor 202 comprises an L-shaped member 210, including an arm segment 212 and a rack segment 214, a second arm segment 216 including a handle 218, and a means for displacing the two arm segments 212,216 with respect to each other responsive to the actuation of the handle 218. As indicated above, in a specific illustrative embodiment, the rack segment 214 is configured with a finochetti type of rack as is known to those skilled in the art. The retractor 202 also includes a plurality of blades 228 at least one blade extending outwardly from a surface, the bottom surface, of each arm segment 212,216.

At least one arm segment and preferably both arm segments 212,216 and/or the rack segment 214 are configured so as to provide at least one mounting point 220 to which a stabilizer support 240 is secured. Preferably, the arm segment and/or the rack segment are configured so as to provide a plurality of such mounting points 220. More particularly, the arms segments 212,216 and/or rack segment 214 are configured with a depressed generally convex surface 222 in the top surface of the arm/rack segment and a corresponding convex surface 224 or arcuate surface on a back surface thereof to form each mounting point 220. Although concave and convex surfaces are illustrated, it is within the scope of the present invention for these surfaces to have generally arcuate shape or similar complementary surfaces. For example, the convex surface on the backside of the arm could be a concave surface.

Slots 226 are formed in a portion of each depressed surface 222 which pass through the convex surface 224. Preferably, the slots 226 form a generally X-shaped pattern in the depressed surface 222 with a through hole centered in the bottom of the depressed surface. However, other slot patterns such a Y-shaped pattern or a star shaped pattern are within the scope of the present invention. Preferably, one of the slots also is arranged so as to extend through the front edge 219 of the arm/rack segment so a portion 263 of a shaft 262 of the sled member 240 can pass therethrough to the centrally located through hole.

The stabilization arm 204 of the present invention includes an arm segment 242 and a stabilizer support or sled member 240. The sled member 240 is configured so the surgeon can position the stabilization device 254 to stabilize the predetermined area. The sled member 240 also is configured so the surgeon, after positioning the stabilization device 254, can secure the stabilization device 254 and the arm segment 242 so the stabilization device remains fixed in this position and the sled member is secured to the retractor 202 without further input or action by the surgeon.

Figure 9:
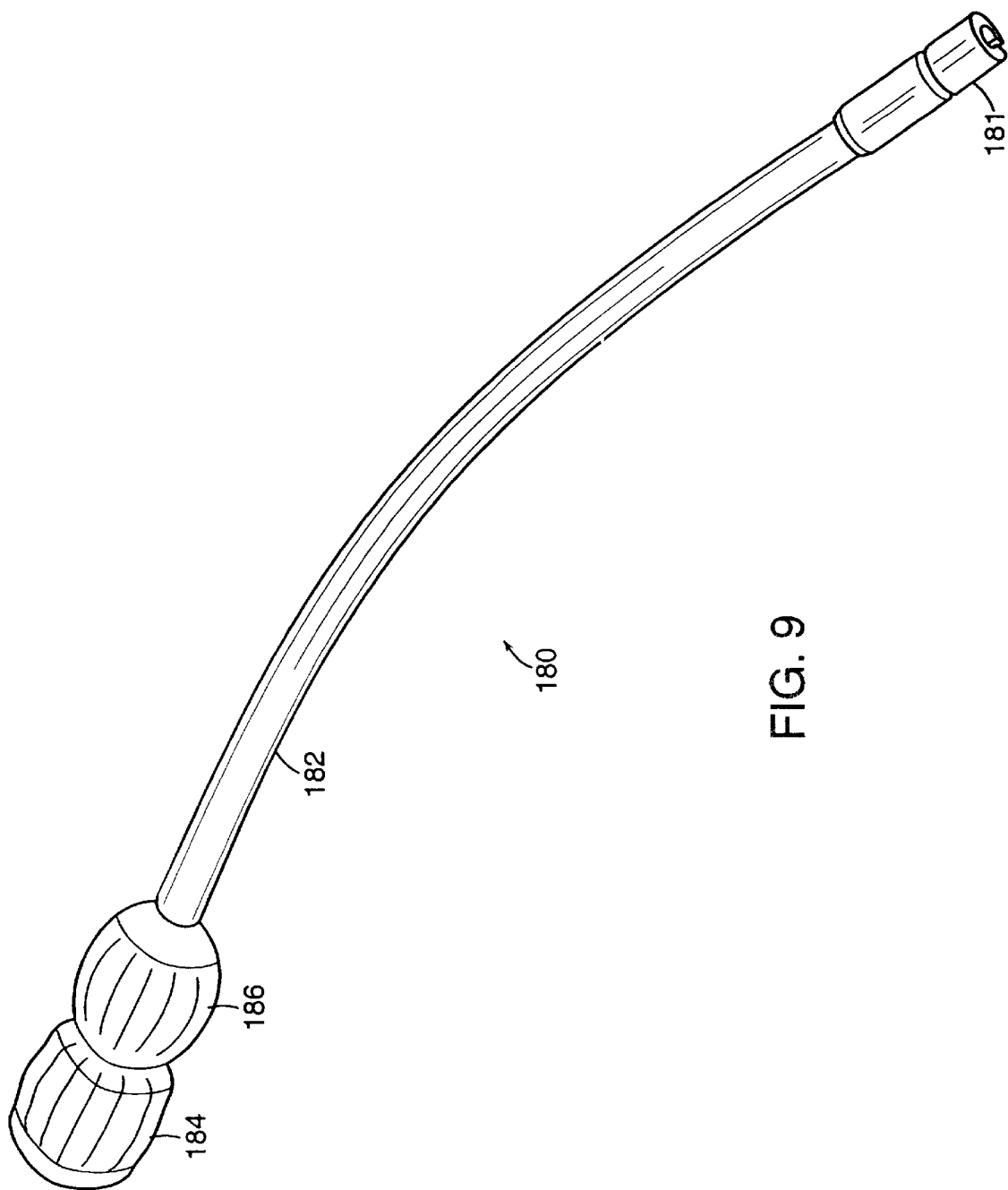
FIG. 9 is a perspective view of a preferred embodiment of the stabilization arm of the present invention.
Figure 10:
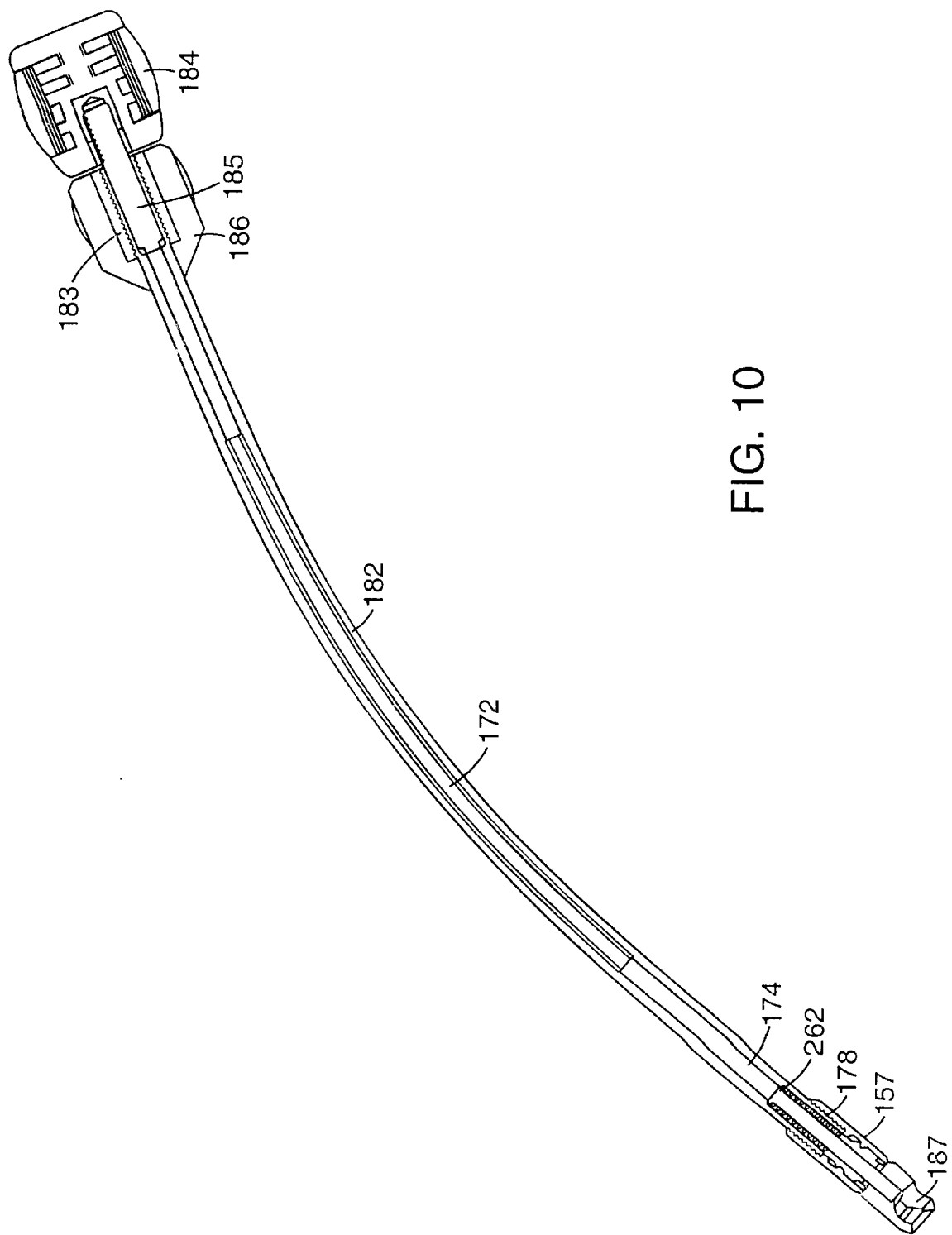
FIG. 10 is a cross section view of the embodiment of FIG. 9.
Figure 11:
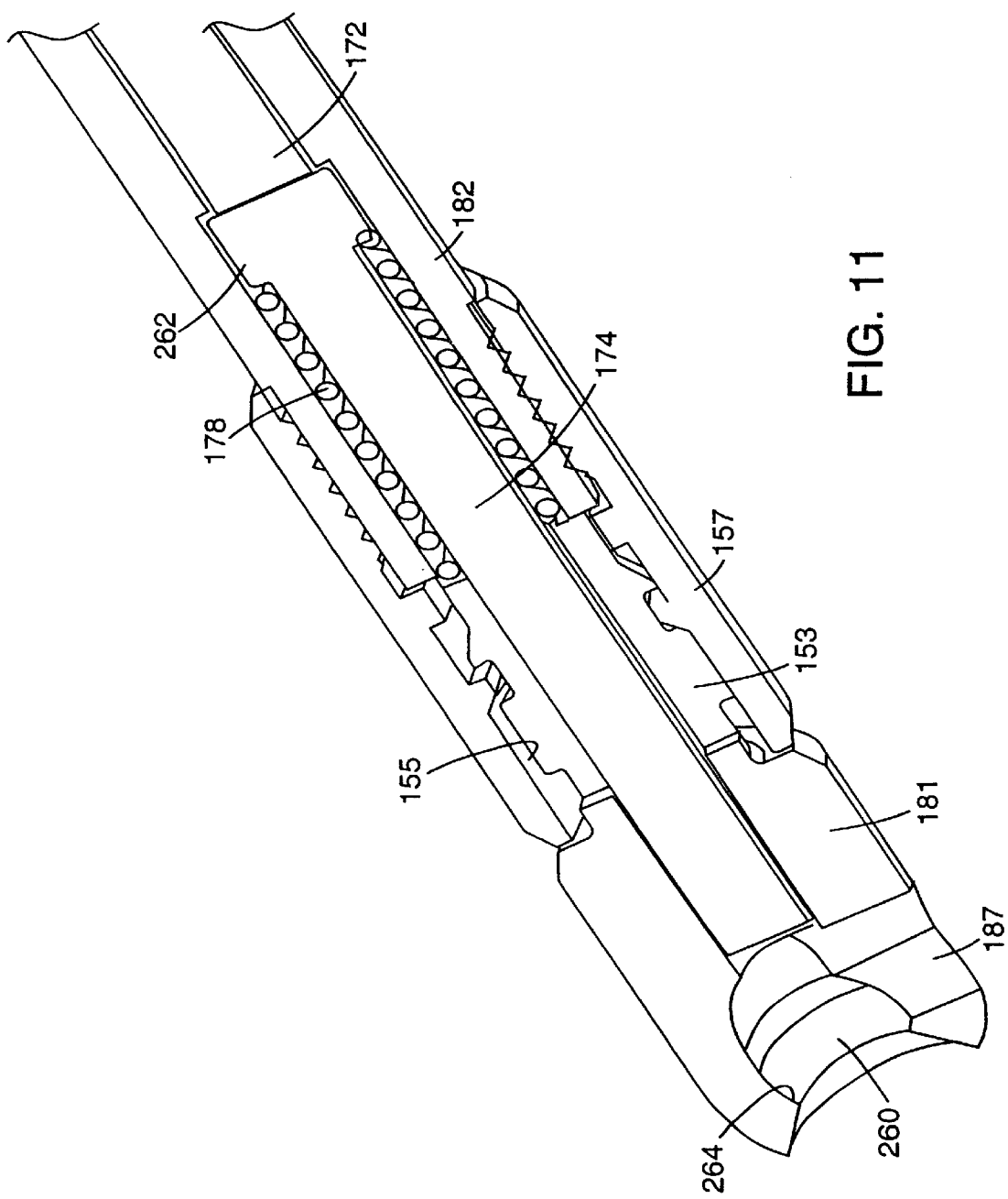
FIG. 11 is an enlarged cross section view showing the distal end portion of the embodiment of FIG. 9.

FIGS. 9–11 illustrate a preferred embodiment of the stabilization arm or sub-system 104 of the present invention. For the sake of brevity, common numbers are used for common elements. In this embodiment, the stabilization system preferably includes a curved and elongate arm segment 180 that interconnects the retractor and the stabilization device. The arm segment 180 preferably includes a first end having a distal connector 181 thereon to pivotally and removably retain the stabilization device thereon. The arm segment 180 is attachable to a retractor by a connector such as a mounting mechanism or sled member. The proximal end of the arm segment 180 preferably includes a movable knob 184 thereon that is rotatable with respect to the arm segment 180 to allow the movement of the stabilization device 106. The movable knob 184 allows the stabilization device 106 to be fixed, removable and/or pivotal with respect to the arm segment 180 by manipulating the movable knob 184 on the proximal end of the arm segment 180. This arrangement also allows the stabilization device to be mountable on and removable from the distal connector 181 such that the stabilization device may be disposable while the stabilization arm may be disposable or reusable.

The arm segment 180 preferably includes a hollow and rigid tubular member 182 that is curved at angle that is chosen to provide the user with increased versatility in the placement of the stabilization device in the desired location while also allowing the longitudinal sliding or movement of the arm segment with respect to the stabilization arm clamp as described in further detail above. The arm segment 180 of this embodiment includes the distal connector 181 on the distal end thereof to pivotally and removably retain post member of the stabilization device thereon. The distal connector 181 of this embodiment is rotatable with respect to the tubular member 182 to further increase the user's ability to orient the arm segment 180 and the stabilization device 106 in the desired position.

The proximal end of the arm segment 180 preferably includes a movable knob 184 and a fixed knob 186 thereon. The movable knob 184 includes a gripping surface thereon and a distally extending portion 185 which is threadedly connected to the proximal end of the arm segment 180. The distally extending portion 185 of the movable knob also includes an end surface thereon that contacts an elongate and movable member 172. The movable member 172 is preferably a rigid member that extends from the proximal end of the arm segment 180, around the curve of the arm segment and to pusher pin 174 of the distal connector 181. The fixed knob 186 is fixed distally of the movable knob 184 and includes a threaded insert 183 therein to receive the distal extending portion 185 of the movable knob 184 therein. The fixed knob 186 on the tubular member 182 allows the user to rotate the stabilization device and arm segment 180 by manipulating the fixed knob 186. Clockwise movement of the movable knob causes the movable member 172 to move distally within the threaded insert 183 of the arm segment 180 while counterclockwise movement of the movable knob causes the movable member 172 to move proximally within the threaded insert 183 of the arm segment 180 as described more fully below.

The distal connector 181 preferably consists of a generally cylindrical or sleeve shaped member having an elongate slot 187 extending through at least one side thereof. The distal connector 181 is preferably rotatable with respect to the arm segment and is retained thereon by a snap fit connection with the distal end of the outer sleeve 157. As shown, the outer sleeve is a cylindrical member that is threadedly attached to the arm segment 180 at the proximal end thereof to prevent movement therebetween while allowing movement between the outer sleeve 157 and the distal connector 181.

The slot 187 of the distal connector 181 is sized to allow the post member of the stabilization device to pass laterally therethrough to allow the stabilization device to be easily mounted on or removed from the stabilization arm 104 through the slot 187. As shown, the distal end of the distal connector includes a central portion 260 that is slightly larger than the rest of the slot surface to allow the post member of the stabilization device to be fully rotatable therethrough. The presence of the central portion 260 increases the range of motion of the stabilization device by preventing the shaft of the post member from binding against the side of the distal connector 181 as the stabilization device is movable through the range of motion during normal use. This arrangement also prevents the post member of the stabilization device from passing distally of the slot 187 while providing a centered position for the post member. This flexibility in positioning allows the surgeon to readily position the stabilization device in the desired position and against nearly any surface of the heart of the patient.

Rotation of the movable knob 184 in a clockwise direction with respect to the arm segment 180 and/or the fixed knob 186 causes the distal movement of the movable member 172 in the tubular member 182. As the movable member 172 is moved distally in the tubular member 182, it contacts the pusher pin 174 located in the distal portion of the arm segment 180. The pusher pin 174 preferably has a generally enlarged ridge surface 262 thereon. The ridge surface 262 contacts a spring member 178 which surrounds the distal portion of the pusher pin 174. The spring member 178 is retained between the ridge member 262 and a lip formed by the proximal end of the inner connector 153. This distal movement of the pusher pin 174 with respect to the tubular member 182 pushes the pusher pin 174 into the slot 187 of the distal connector 181 to press against the post member of the stabilization device. The distal movement of the pusher pin 174 against the post member causes the post member 196 to press against the lower lip surfaces 264 adjacent to the central opening on the distal surface of the slot 187 of the distal connector 181. The distal movement of the pusher pin 174 also prevents rotation of the distal connector 181 relative to the arm segment 180 by increasing the frictional resistance between the inner connector 153 and groove 155.

Rotation of the movable knob 184 in a counterclockwise direction with respect to the arm segment 180 and/or the fixed knob 186 causes the distally extending member 185 to move proximally in the threaded insert 183 of the tubular member 182. As this occurs, the spring member 178 pushes against the ridge surface 262 of the pusher pin 174 and causes the distal end of the pusher pin 174 to move proximally away from the slot 187. This proximal movement of the distal end of the pusher pin 174 allows for the rotation and/or release of the post member of the stabilization device from the distal connector 181.

The generally cylindrical shape of the distal connector 181 and the opening in the slot 187 optimize the connection between the distal connector 181 of the arm and the post member of the stabilization device. This arrangement enables the post member to be selectively retained within the distal connector 181 while allowing pivotal and rotational movement therebetween. This increased versatility allows the user to further manipulate the handle member and stabilization device to the desired location in the surgical field. This freedom of movement and versatility is desirable for the present invention where space is at a premium and the device must be as versatile as possible to accommodate the surgeons needs without undue experimentation.

In the foregoing discussion, the stabilization system of the present invention is described in terms of clamping and supporting a stabilization device. It is within the scope of the present invention, however, for the system to be configured to removably secure any of a number of surgical instruments to the retractor or similar device such as for example diaphragm or valve retractors. Additionally, although one stabilization arm is described as being in use at a time, it is within the scope of the present invention for plurality or a multiplicity of stabilization arms to be secured to the retractor. For example, one stabilization arm could be provided to support a diaphragm retractor and another stabilization arm provided to support a tissue stabilizer or suction device.

Although a preferred embodiment of the invention has been described using specific terms, such description is for illustrative purposes only, and it is to be understood that changes and variations may be made without departing from the spirit or scope of the following claims.

What is claimed is:

1. A system for use in a surgical procedure on a human patient, comprising:
   a retractor having a plurality of retractor arms thereon and a segment interconnecting said retractor arms wherein said retractor arms are movable with respect to each other;
   a curved stabilization arm operatively positionable with respect to said retractor and said stabilization arm being sized to hold a medical device in a desired position during a medical procedure;
   a stabilization device operatively positioned on said stabilization arm;
   wherein said stabilization arm includes an elongate tubular member having a movable member and a spring member therein and wherein said spring member biases said movable member towards a position that is spaced apart from said stabilization device; and
   a connector which is selectively mountable on said retractor.

2. The system of claim 1 wherein said stabilization arm has an angle of curvature of less than 30 degrees.

3. The system of claim 1 wherein said curved stabilization arm has an angle of curvature that may be oriented upwardly or downwardly with respect to said retractor.

4. The system of claim 1 wherein said stabilization arm includes a distal end portion and a proximal end portion wherein said distal end portion includes said stabilization device removably mounted thereon.

5. The system of claim 1 wherein said stabilization arm includes at least one movable knob member and a distal end portion and a proximal end portion thereon wherein said distal end portion includes said stabilization device mounted thereon and actuation of said movable member affects the movement of said stabilization device on said distal end portion of said stabilization arm.

6. The system of claim 5 wherein movement of said movable knob member causes the distal and proximal movement of a pin member and said pin member contactingly engages a portion of said stabilization device in one of the distal and proximal movements thereof.

7. The system of claim 6 wherein said pin member thereon is movable between engaged and disengaged positions to engage and disengage said stabilization device from said stabilization arm.

8. A system for use in a surgical procedure on a human patient, comprising:
   a retractor having a plurality of retractor arms thereon and a segment interconnecting said retractor arms wherein said retractor arms are movable with respect to each other;
   a curved stabilization arm operatively positionable with respect to said retractor and said stabilization arm being sized to hold a medical device in a desired position during a medical procedure;
   a stabilization device operatively positioned on said stabilization arm;
   a connector which is selectively mountable on said retractor
   wherein said stabilization arm includes a distal end portion and a proximal end portion wherein said distal end portion includes said stabilization device removably mounted thereon; and
   wherein said stabilization arm includes an elongate tubular member having a plurality of ball members therein and said ball members are movable in the tubular member in response to the movement of a movable knob member on the proximal end portion of the stabilization arm.

9. A system for use in a surgical procedure on a human patient, comprising:
   a retractor having a plurality of retractor arms thereon and a segment interconnecting said retractor arms wherein said retractor arms are movable with respect to each other;
   a curved stabilization arm operatively positionable with respect to said retractor and said stabilization arm being sized to hold a medical device in a desired position during a medical procedure;
   a stabilization device operatively positioned on said stabilization arm;
   a connector which is selectively mountable on said retractor;
   wherein said stabilization arm includes a distal end portion and a proximal end portion wherein said distal end portion includes said stabilization device removably mounted thereon;
   wherein movement of said movable knob member causes the distal and proximal movement of a pin member and said pin member contactingly engages a portion of said stabilization device in one of the distal and proximal movements thereof;
   wherein said pin member thereon is movable between engaged and disengaged positions to engage and disengage said stabilization device from said stabilization arm; and
   wherein said pin member extends into a slot member located on the distal end portion of the stabilization arm in the engaged position and is spaced apart therefrom in the disengaged position.

10. A system for use in a surgical procedure on a human patient, comprising:
   a retractor having a plurality of retractor arms thereon and a segment interconnecting said retractor arms wherein said retractor arms are movable with respect to each other;
   a curved stabilization arm operatively positionable with respect to said retractor and said stabilization arm being sized to hold a medical device in a desired position during a medical procedure;
   a stabilization device operatively positioned on said stabilization arm;
   a connector which is selectively mountable on said retractor;
   wherein said stabilization arm includes a distal end portion and a proximal end portion wherein said distal end portion includes said stabilization device removably mounted thereon;
   wherein movement of said movable knob member causes the distal and proximal movement of a pin member and said pin member contactingly engages a portion of said stabilization device in one of the distal and proximal movements thereof;

wherein said pin member thereon is movable between engaged and disengaged positions to engage and disengage said stabilization device from said stabilization arm; and wherein said pin member moves between said engaged and disengaged positions in response to a spring member that is biased to cause said pin member to be spaced apart from said stabilization device.

11. A system for use in a surgical procedure, comprising:

a retractor having a plurality of retractor arms thereon and a segment interconnecting said retractor arms wherein said retractor arms include a front edge surface and are movable with respect to each other;

a curved stabilization arm having distal and proximal end portions and said stabilization arm is operatively positionable with respect to said retractor and sized to hold a medical device in a desired position during a medical procedure;

wherein said stabilization arm includes an elongate tubular member having a movable member and a spring member therein and wherein said spring member biases said movable member to be oriented to move away from said stabilization device; and a connector which is attachable in a fixed position on said retractor and which interacts with said stabilization arm to position said distal end portion of said stabilization arm and said medical device is movable to a position below and behind said front edge surface of one of said retractor arms.

12. The system of claim 11 wherein said stabilization arm has an angle of curvature of less than 30 degrees.

13. The system of claim 11 wherein said distal end portion of said stabilization arm is rotatable with respect to said proximal end of said stabilization arm.

14. The system of claim 11 wherein said stabilization arm includes a removable stabilization device on the distal end portion thereof.

15. The system of claim 14 wherein actuation of a member on said proximal end portion of said stabilization arm affects the movement of said stabilization device on said distal end portion of said stabilization arm.

16. The system of claim 11 wherein actuation of a member on said proximal end portion of said stabilization arm causes the longitudinal movement of a movable member in said stabilization arm to affect the movement of said stabilization device on said distal end portion of said stabilization arm.

17. A system for use in a surgical procedure, comprising:

a retractor having a plurality of retractor arms thereon and a segment interconnecting said retractor arms wherein said retractor arms include a front edge surface and are movable with respect to each other;

a curved stabilization arm having distal and proximal end portions and said stabilization arm is operatively positionable with respect to said retractor and sized to hold a medical device in a desired position during a medical procedure;

a connector which is attachable in a fixed position on said retractor and which interacts with said stabilization arm to position said distal end portion of said stabilization arm and said medical device is movable to a position below and behind said front edge surface of one of said retractor arms;

wherein actuation of a member on said proximal end portion of said stabilization arm causes the longitudinal movement of a movable member in said stabilization arm to affect the movement of said stabilization device on said distal end portion of said stabilization arm; and wherein said movable member includes a plurality of ball members contained in an elongate tubular portion of said stabilization arm and wherein the ball members are movable in the elongate tubular portion in response to actuation of the member on the proximal end portion of the stabilization arm.

18. A system for use in a surgical procedure, comprising:

a retractor having a plurality of retractor arms thereon and a segment interconnecting said retractor arms wherein said retractor arms include a front edge surface and are movable with respect to each other;

a curved stabilization arm having distal and proximal end portions and said stabilization arm is operatively positionable with respect to said retractor and sized to hold a medical device in a desired position during a medical procedure;

a connector which is attachable in a fixed position on said retractor and which interacts with said stabilization arm to position said distal end portion of said stabilization arm and said medical device is movable to a position below and behind said front edge surface of one of said retractor arms;

wherein actuation of a member on said proximal end portion of said stabilization arm causes the longitudinal movement of a movable member in said stabilization arm to affect the movement of said stabilization device on said distal end portion of said stabilization arm; and wherein said tubular portion of said stabilization arm includes a spring member therein that is biased to cause said movable member to be spaced apart from said stabilization device.

19. A system for use in a surgical procedure, comprising:

a retractor having a plurality of retractor arms thereon and a segment interconnecting said retractor arms wherein said retractor arms include a front edge surface and are movable with respect to each other;

a curved stabilization arm having distal and proximal end portions and said stabilization arm is operatively positionable with respect to said retractor and sized to hold a medical device in a desired position during a medical procedure;

a connector which is attachable in a fixed position on said retractor and which interacts with said stabilization arm to position said distal end portion of said stabilization arm and said medical device is movable to a position below and behind said front edge surface of one of said retractor arms;

wherein actuation of a member on said proximal end portion of said stabilization arm causes the longitudinal movement of a movable member in said stabilization arm to affect the movement of said stabilization device on said distal end portion of said stabilization arm; and wherein movement of said movable member causes a pin member to move between engaged and disengaged positions relative to said stabilization device and said pin member is biased to be spaced apart from said stabilization device.

\* \* \* \* \*